US008401874B2

(12) United States Patent
Rosenfeld

(10) Patent No.: US 8,401,874 B2
(45) Date of Patent: *Mar. 19, 2013

(54) RULES-BASED SYSTEM FOR MATERNAL-FETAL CARE

(75) Inventor: Brian A. Rosenfeld, Baltimore, MD (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 427 days.

This patent is subject to a terminal disclaimer.

(21) Appl. No.: 12/397,536

(22) Filed: Mar. 4, 2009

(65) Prior Publication Data

US 2009/0216564 A1    Aug. 27, 2009

Related U.S. Application Data

(63) Continuation-in-part of application No. 11/072,359, filed on Mar. 4, 2005, now Pat. No. 8,175,895, which is a continuation-in-part of application No. 10/654,668, filed on Sep. 4, 2003, now Pat. No. 7,475,019, and a continuation-in-part of application No. 10/946,548, filed on Sep. 21, 2004, now Pat. No. 7,256,708, which is a continuation-in-part of application No. 09/443,072, filed on Nov. 18, 1999, now Pat. No. 6,804,656.

(60) Provisional application No. 60/141,520, filed on Jun. 23, 1999.

(51) Int. Cl.
*G06Q 50/00* (2012.01)
(52) U.S. Cl. .................................. 705/3; 705/2; 600/300
(58) Field of Classification Search .................. 705/2–3; 600/300
See application file for complete search history.

(56) References Cited

U.S. PATENT DOCUMENTS 6,101,478 A * 8/2000 Brown ............................. 705/2
6,329,139 B1 * 12/2001 Nova et al. ...................... 506/30

* cited by examiner

*Primary Examiner* — Sind Phongsvirajati

(57) ABSTRACT

A rules-base patient care method for managing the care of a plurality of pregnant patients from a remote command center for use in healthcare locations using patient-specific rules for each of the plurality of pregnant patients. A patient rules generator creates rules for the patients. Performance measures indicative of the ability of a rule to predict changes in the condition of the patient are acquired by the rules generator. A determination is made from the rules performance measures whether to revise the rule. A rules engine applies a rule to selected data elements stored in the database to produce an output indicative of a change in the medical condition of a pregnant patient and/or a fetal patient. The output from the rules engine is used to determine when intervention is warranted.

44 Claims, 14 Drawing Sheets

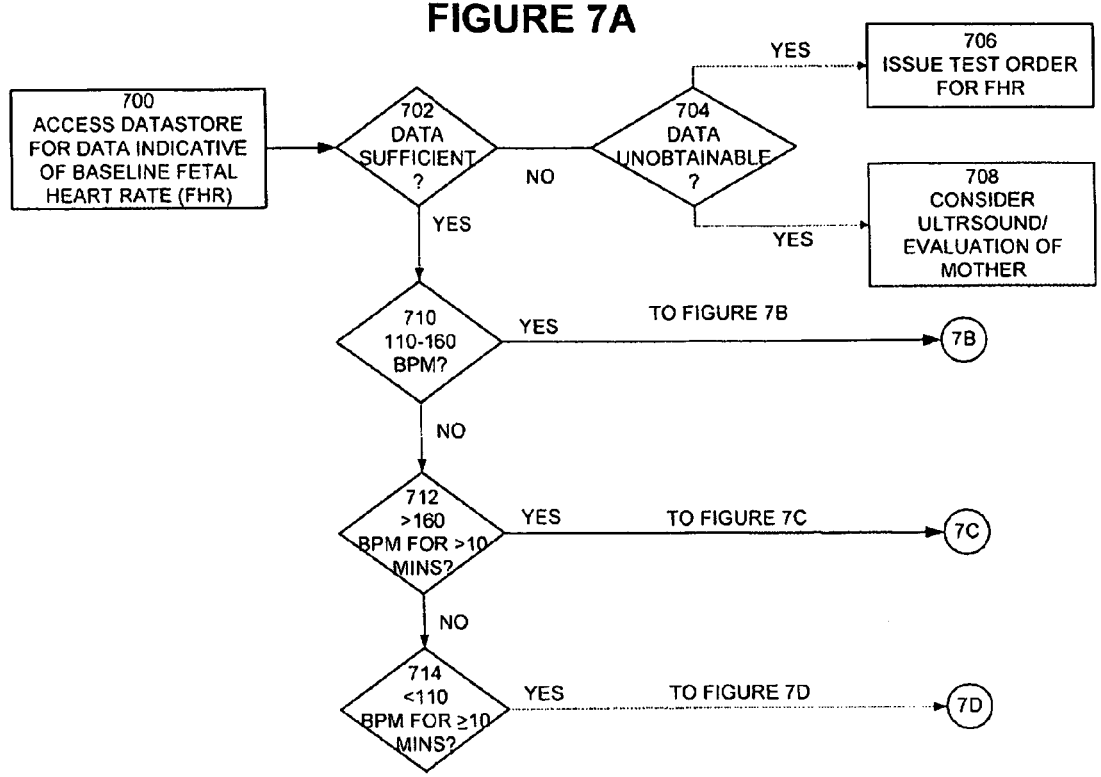

RULES-BASED SYSTEM FOR MATERNAL-FETAL CARE

RELATIONSHIP TO OTHER APPLICATIONS

This application is a continuation-in-part of application Ser. No. 11/072,359 filed Mar. 4, 2005, which is a continuation-in-part of application Ser. No. 10/654,668 filed Sep. 4, 2003, now U.S. Pat. No. 7,475,019 and a continuation in part of application Ser. No. 10/946,548 filed Sep. 21, 2004, now U.S. Pat. No. 7,256,708, both of which are continuations-in-part of application Ser. No. 09/443,072 filed Nov. 18, 1999, now U.S. Pat. No. 6,804,656 issued Oct. 12, 2004, which claims the benefit of U.S. Provisional Application No. 60/141,520, filed Jun. 23, 1999. The Ser. Nos. 11/072,539, 10/654,668, 10/946,548, 09/443,072, and the 60/141,520 applications are hereby incorporated by reference in their entirety for all purposes.

BACKGROUND

Embodiments of this invention relate generally to providing care to patients in healthcare locations. More particularly, embodiments of this invention provide a system and method for treating a pregnant woman and/or her fetus using a rules-based system and method.

Perinatology is a subspecialty of obstetrics that deals with the care of the mother and fetus at higher-than-normal risk for complications. A patient may be referred to a perinatologist if her fetus has a suspected or known abnormality, an abnormal karyotype (such as Down syndrome), or a maternal condition which may affect the fetus. Risk factors that may lead to care by a perintatologis include:
- maternal/family history of cardiac disease
- a known or newly diagnosed history of hypertension (high blood pressure)
- preeclampsia (toxemia)
- maternal metabolic diseases, including diabetes (both pregestational and gestational types)
- infectious diseases (to include parvovirus, toxoplasmosis, hepatitis, HIV, and AIDS)
- maternal/family history of renal, gastrointestional disease, and cystic fibrosis
- an abnormal AFP (alpha fetoprotein) blood test (including the suspicion of a neural tube defect)
- an abnormal triple screen (including the suspicion of a chromosomal abnormality such as Trisomy 21 (Down syndrome), Trisomy 13 or Trisomy 18)
- multiple gestation (twins and higher order multiples)
- poor past obstetrical history (to include past preterm deliveries, preterm labor, preterm cervical dilatation, premature rupture of membranes, repetitive pregnancy loss)
- suspected abnormal fetal growth—both macrosomia (a baby that is too large) or fetal growth restriction (a baby that is too small)
- maternal lupus
- red cell alloimmunization (Rh– mother sensitized to an Rh+ fetus)
- the need for invasive fetal testing/procedures such as:
    - fetal blood sampling/transfusion or other type of in utero therapeutic procedure(s)
    - the need for chorionic villus sampling (CVS) or amniocentesis (amnio) for maternal age or other factors
- a known/suspected fetal anomaly
- the need for genetic counseling services
- the need for antepartum fetal testing Advances in communications, video displays, monitoring devices and computers have made it possible to remotely monitor hundreds of monitored patients. Alerting systems may be deployed to alert healthcare providers when certain conditions are met. For example, in U.S. Pat. No. 5,942,986 issued to Shabot, et. al for a "System And Method For Automatic Critical Event Notification," describes a critical event notification system that permits review of a patient's diagnostic information, lab results, chart, or other data, automatically, by computer or similar equipment, and it provides for automatic paging of a responsible physician or physicians should a "critical event" be detected. The decision to page an individual is made automatically by the system, and does not require a direct human decision.

"Decision Support Systems in Critical Care" (Edited by M. Michael Shabot and Reed M. Gardner, 1994), is a compilation of articles that collectively describe the application of computers in health care settings. Decision support systems are defined as systems that receive medical data as input and produce medical information and/or knowledge as output. In some implementations, decision support systems utilize inferencing methods to detect associations between different pieces of information, alerting clinicians to certain patterns of events, which may be serious or life-threatening.

An example implementation of an inferencing method is described in the context of analyzing blood gas readings and laboratory results. Three different types of alerting algorithms are described: 1) high and low critical values 2) calculation-adjusted critical values, and 3) critical trends. (See, Decision Support Systems in Critical Care, pages 157-65.) The calculation-adjusted critical value algorithm reflects the dependence of the algorithm on multiple parameters. The application of the inferencing module produces an alert that is displayed on a screen or sent to a wireless device.

In U.S. Pat. No. 6,804,656 issued to Applicants, a smart alarm system was described. The smart alarm system of the '656 patent, constantly monitors physiologic data and all other clinical information stored in the database (labs, medications, etc). The rules engine searches for patterns of data indicative of clinical deterioration. By way of illustration, one family of alarms looks for changes in vital signs over time, using pre-configured thresholds. These thresholds (also referred to as "rules") are patient-specific and setting/disease-specific. Physiologic alarms can be based on multiple variables. For example, one alarm looks for a simultaneous increase in heart rate of 25% and a decrease in blood pressure of 20%, occurring over a time interval of 2 hours. Alarms also track additional clinical data in the patient database. Other rules follow laboratory data (e.g. looking for need to exclude active bleeding and possibly to administer blood). Regardless of the data elements that are used, the purpose of the rules is to facilitate detection of changes in a patient's condition (whether that condition is improving or degrading) in a predictive manner and to automate a response appropriate to the "new" condition.

Clinical prediction has been practiced in various forms since the first doctor practiced medicine. Observation, intuition, and the prevailing wisdom of the time were used to diagnose and treat illness. The patient's status following a particular treatment was associated with the treatment, whether or not there was a causal connection between the two. Often, treatments that were ineffective, or worse, deleterious, were perpetuated because there was not basis for determining whether there was a cause and effect relationship between the treatment and the result.

Scoring systems were developed to identify the important physiologic parameters and chronic health conditions that determine clinical outcome. The typical clinical prediction rule is geared to determine a specific outcome. The identification of the key predictive variables is accomplished using well-known statistical techniques. The model is validated by applying the scoring system to patients and confirming the outcome against the predicted outcome.

An example of a predictive scoring system is the Acute Physiologic and Chronic Health Evaluation II (APACHE II) instrument commonly used to assess patients for admission to an ICU. The APACHE II instrument studied 5800 patients, and 13 hospitals, and, with statistical methods, identified 12 continuous physiologic variables measured within twenty-four hours of ICU admission." These variables were coupled with others describing the chronic health of the patient. APACHE II has also been applied to a wide variety of clinical issues in critical care and has been the method of choice for describing the severity of illness in some landmark studies.

APACHE II has several unintended flaws. The first was that the derivation data set was relatively small and therefore did not have the statistical power to describe subsets of disease, such as congestive heart failure, liver failure, and hematologic malignancy. The second was that the instrument would not distinguish between patients who had prior treatment and those who did not. This flaw, now termed "lead-term bias," was discovered when a number of investigators demonstrated that the predictive accuracy of APACHE II faltered when it was applied to patients who were transferred from other ICUs or from within the hospital setting. In these situations, the APACHE II instrument underestimated mortality.

APACHE III was intended to correct this deficiency. This instrument was derived from 17,440 patients, and 40 hospitals, representing a wider spectrum than APACHE II. APACHE III employs 17 continuous physiologic variables, chronic health information, prior treatment location before ICU admission, and principal ICU diagnosis. It also has a new feature whereby mortality prediction is updated on a continuous basis.

A Simplified Acute Physiologic Score (SAPS) was developed to streamline the approach utilized by the APACHE systems. The SAPS II system employs 17 variables: 12 categorical physiologic variables; age; type of admission; and three other designated disease variables (acquired immunodeficiency syndrome or AIDS, metastatic cancer, and hematologic malignancy). The SAPS score is entered into a mathematical formula, which can be solved on a calculator and whose solution provides the predicted hospital mortality. Therefore no commercial computer software is necessary to perform this calculation. This simplicity plus its low cost have made SAPS a popular choice in some centers, particularly in Europe.

The Mortality Prediction Model (MPM) uses a mathematical formula whose solution provides a prediction of patient mortality. Typically, the MPM score is determined immediately upon ICU admission. The updated version of MPM (MPM24) uses a score twenty-four hours after ICU admission, utilizing five of the admission variables and eight additional physiologic variables. This provides two points of prognostic assessment within a 24-hour period. The MPM24 correlates with SAPS and APACHE, since all three are measured within twenty-four hours of ICU admission.

Many other predictive models have been developed for various purposes. By way of illustration and not as a limitation, a partial list of predictive models comprises SAPS II expanded and predicted mortality, SAPS II and predicted mortality, APACHE II and predicted mortality, SOFA (Sequential Organ Failure Assessment), MODS (Multiple Organ Dysfunction Score), ODIN (Organ Dysfunctions and/or INfection), MPM (Mortality Probability Model), MPM II LODS (Logistic Organ Dysfunction System), TRIOS (Three days Recalibrated ICU Outcome Score), EUROSCORE (cardiac surgery), ONTARIO (cardiac surgery), Parsonnet score (cardiac surgery), System 97 score (cardiac surgery), QMMI score (coronary surgery), Early mortality risk in redocoronary artery surgery, MPM for cancer patients, POSSUM (Physiologic and Operative Severity Score for the enUmeration of Mortality and Morbidity) (surgery, any), Portsmouth POSSUM (surgery, any), IRISS score: graft failure after lung transplantation, Glasgow Coma Score, ISS (Injury Severity Score), RTS (Revised Trauma Score), TRISS (Trauma Injury Severity Score), ASCOT (A Severity Characterization Of Trauma), 24 h—ICU Trauma Score, TISS (Therapeutic Intervention Scoring System), TISS-28 (simplified TISS), PRISM (Pediatric RISk of Mortality), P-MODS (Pediatric Multiple Organ Dysfunction Score), DORA (Dynamic Objective Risk Assesment), PELOD (Pediatric Logistic Organ Dysfunction), PIM II (Paediatric Index of Mortality II), PIM (Paediatric Index of Mortality), CRIB II (Clinical Risk Index for Babies), CRIB (Clinical Risk Index for Babies), SNAP (Score for Neonatal Acute Physiology), SNAP-PE (SNAP Perinatal Extension), SNAP II and SNAPPE II, MSSS (Meningococcal Septic Shock Score), GMSPS (Glasgow Meningococcal Septicaemia Prognostic Score), Rotterdam Score (meningococcal septic shock), Children's Coma Score (Raimondi), Paediatric Coma Scale (Simpson & Reilly), and Pediatric Trauma Score.

Rules-based systems and predictive modeling systems are typically applied to a viable patient after birth. What would be useful would be a system and method for applying rules and predictive models to a pregnant woman and/or her fetus during the period defined by the onset of labor and the birth of a baby.

SUMMARY

An embodiment of the present invention uses a telecommunications network to facilitate rules-based care of patients receiving perinatologic care in a healthcare location. In this embodiment, "patients" encompasses a pregnant woman patient (herein, the "mother patient") and the unborn fetal patient (herein, the "fetal patient"). As used herein, a healthcare location may be a remote clinic, a doctor's office, a field hospital, a disaster aid station, a patient transport vehicle and similar care facilities. The patients may be selected for monitoring based on criteria established for the woman patient, the fetal patient or both. In this context of this application monitoring is not limited to the receipt of data from equipment that is physically or eclectically connected to the patient. Rather, monitoring is broadly comprises retrieving or receiving data from such equipment, as well as patient monitoring data from lab tests, physicians notes, initial diagnoses, and any other information that informs and assists a healthcare provider in caring for a patient. Some of this data is streaming data in real or near real time, while other data comes in as it is generated and may not necessarily be on any fixed timetable for receipt. Such data may be time driven or event driven.

Patient monitoring equipment acquires monitored data elements from both the mother patient and the fetal via patient monitoring station and transmits the monitoring data over a network to a remote command center. Monitored data comprises physiological data elements, video data elements, and audio data elements. The remote command center receives the monitoring data from all patient monitoring stations. The remote command center also accesses other data relating to the condition of either or both patients. By way of illustration and not as limitation, the remote command center has access to data relating to personal information about the mother patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare location. The remote command center may also have information about the fetal patient. By way of illustration and not as a limitation, the remote command center may have access to the medical history of the fetus (size, growth rate, orientation in the uterus, gender), medical history (injuries, surgeries), and laboratory results (genetic tests, blood tests, fetal heart rate tests, amniocentesis). The data available to the remote command center over the network, that is, the monitoring data and the patient data, are collectively referred to as "assessment data."

A rules engine applies a rule or rule set to the data elements selected from the assessment data from each monitored patient to determine whether the rule for that patient has been contravened. A mother-specific rule may require monitored data of the fetal patient, and a fetal-specific rule may require monitored data of the mother patient. In the event a rule has been contravened, an alert at the remote command center is triggered. Rules for the mother patient and the fetal patient may be established and changed at the remote command center for each patient as the patients' conditions warrant. In one embodiment of the present invention, a rule is established to determine whether a patient's condition is deteriorating. In another embodiment, a rule is established to determine whether a patient's condition is improving. In yet another embodiment of the present invention, an alert that a rule has been contravened comprises advice on treatment of the patient.

A patient rules generator establishes one or more rules for the monitored patient associated with a patient monitoring station. The patient rules generator collects rules performance measures indicative of the ability of the rule to predict changes in the condition of a patient and uses these measures to assess the efficacy of the rule. The patient rules generator may update a rule, determine that a rule is acceptable as is, or determine that there is insufficient data to revise a rule.

The patient rules generator may also evaluate the assessment data of patients with similar conditions to determine whether a predictive rule can be written and applied to patients with the same or similar conditions. The patient rules generator may also test a proposed rule against historical data to determine whether the rule is predictive of a change in a patient's condition.

Another embodiment of the present invention provides continued care software that uses elements of the assessment data to provide decision support and that prompts a user for input to provide decision support to caregivers. A decision support algorithm responds to elements of assessment data to produce textural material describing a medical condition, scientific treatments and possible complications. This information is available in real time to assist in all types of clinical decisions from diagnosis to treatment to triage.

In still another embodiment of the present invention, order writing software facilitates the ordering of procedures and medications using patient-specific data. The order writing software and the continued care software are interactive allowing a caregiver to access features of both applications simultaneously, so that patient orders are given that are consistent and not conflicting with a patient's status and condition (i.e., allergies to medications or medications that may conflict with the order in question).

In an embodiment of the present invention, a healthcare location patient care system provides care to healthcare location patients based on the capabilities of the healthcare location. In this embodiment, the rules generator, the rules engine, the decision support algorithms, the order writing software facilities, and the continued care software are adapted to the capabilities of the healthcare location based on the application of site assessment rules to the healthcare location. In another embodiment of the present invention, components of a healthcare location patient care system may be supplied to the healthcare location to improve the level of its treatment capabilities. In still another embodiment of the present invention, components of the healthcare location are packaged and assigned a site assessment code. The code is used by the remote command center to predetermine elements of the site assessment process thereby simplifying that process.

In another embodiment of the present invention, patient monitoring equipment acquires monitored data elements from a patient monitoring station and stores monitoring data locally. The stored monitoring data is sent to a remote command center along with patient data at a pre-established time or when requested by remote command center. The remote command center evaluates the "delay" monitored data and assessment data in the same manner as if these data were received in real time. By way of illustration, the remote command center will apply the rules engine and the decision support algorithms to the delayed monitored data and patient data and provide guidance to the healthcare location. This embodiment of the present invention thus provides high quality care in environments where continuous high bandwidth communications are not available or economically infeasible.

In still another embodiment of the present invention, the delivery of stored monitoring data and patient data is expedited by an urgent consultation warning system (herein, the UCWS). The UCWS constantly evaluates the monitoring data and patient data before those data are stored to determine if an urgent consultation is warranted. By way of illustration and not as a limitation, changes in hemodynamic and respiratory measures over time indicative of a degrading condition of a patient would trigger an immediate reporting of all stored monitored and patient data to the remote command center for evaluation.

In an embodiment of the present invention, a rules-based patient care system comprises a network, a database accessible via the network, a rules engine connected to the network, and a patient rules generator connected to the network. By way of illustration and not as a limitation, the network may be a wired network, a wireless network, a satellite network, a public switched telephone network, an IP network, a packet switched network, a cell phone network, a cable network, a coax network, and a hybrid fiber coax network.

The database comprises patient data elements indicative of a medical condition associated with a patient. The rules engine applies a patient rule to selected data elements stored in the database to produce an output indicative of a change in the medical condition of the patient. In various embodiments of the present invention, the selected data elements comprise: a physiological data element of the patient and a clinical data element of the patient, a physiological data element of the patient and a medication data element of the patient, a physiological data element of the patient and a laboratory data element of the patient, a clinical data element of the patient and a laboratory data element of the patient, and a physiological data element of the patient and another physiological data element of the patient. In another embodiment of the present invention, the selected data elements comprise at least two data elements of the patient selected from the group consisting of a physiological data element, a clinical data element of the patient, a medication data element of the patient, and a laboratory data element of the patient. In still another embodiment of the present invention, patient data elements are selected from the group consisting of physiological data elements and clinical data elements.

The output of the rules generator is used to determine if intervention is warranted. In an embodiment of the present invention, the patient data elements indicative of the change in the medical condition of the patient comprise data indicative of improvement of the condition of the patient. In another embodiment of the present invention, the data indicative of the change in the medical condition of the patient comprise data indicative of degradation of the condition of the patient.

In another embodiment of the present invention, intervention comprises issuing a patient intervention protocol and order. In yet another embodiment of the present invention, intervention comprises issuing a patient release protocol and order.

The patient rules generator creates the patient rule, acquiring rules performance measures indicative of the ability of the rule to predict the change in the condition of the patient, and determining from the rules performance measures whether to revise the rule. In an embodiment of the present invention, the patient rule comprises an algorithm.

In an embodiment of the present invention, the rules performance measures are derived from information provided by health care providers. By way of illustration and not as a limitation, doctors, nurses, intensivists, surgeons, and laboratory technicians may provide information relating to the performance of a rule.

In another embodiment of the present invention, the patient rules generator accesses historical data, applying multivariate analyses to the historical data to produce a result that relates the other patient data elements, the rule, and the other patient outcomes, and generating a rules performance measure comparing the result to the patient rule. In another embodiment of the present invention, historical data comprises other patient data elements for a plurality of other patients and wherein the patient data elements of an other patient are associated with an outcome of the other patient.

In still another embodiment of the present invention, the patient rules generator generates a new rule from the result. In yet another embodiment of the present invention, the patient rules generator tests the new rule against the historical data.

In an embodiment of the present invention, the rules-based patient care system further comprises a site assessment module. The site assessment module receives site assessment data and determining from the site assessment data service level measures indicative of a capability of a healthcare location to provide diagnostic and treatment services to patients. In this embodiment, the rules generator receives service level measures, and creating the patient rule consistent with the service level measures. In another embodiment of the present invention the site assessment data are indicative of the capability of the healthcare location to provide diagnostic and treatment services to patients.

In yet another embodiment of the present invention, the site assessment module prompts a user for the site assessment data and determining the service level measures based on the user response.

In an embodiment of the present invention, the healthcare location is associated with site assessment code and the site assessment module acquires the site assessment code associated with the healthcare location, and determining the service level measures at least in part based on the site assessment code.

In still another embodiment of the present invention, the service level measures comprise an inventory of available monitoring data elements, an inventory of available diagnostic services, an inventory of available surgical treatment services, and an inventory of available laboratory services.

DESCRIPTION OF THE FIGURES

FIGS. 7A, 7B, 7C, 7D and 7E illustrate an application of a decision support algorithm for fetal well-being to patient data according to an embodiment.

DETAILED DESCRIPTION

Figure 1:
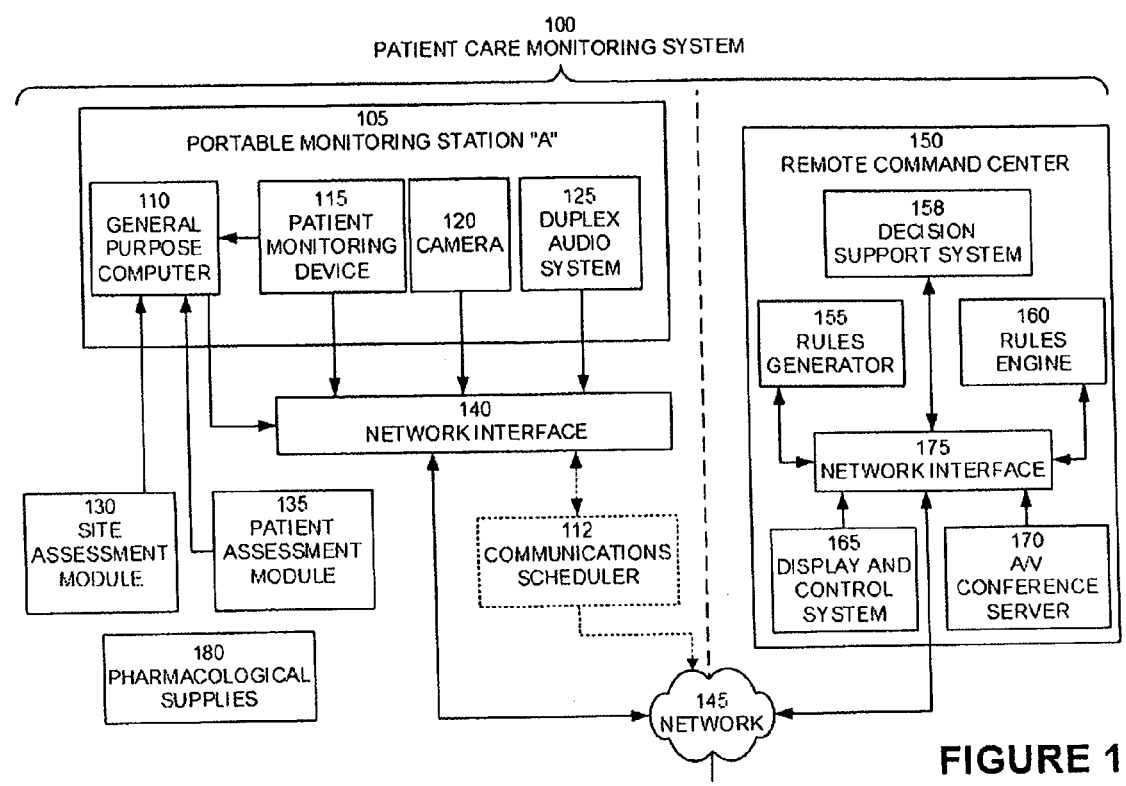
FIG. 1 illustrates a block diagram of the components of a monitored patient care system (HPCS) according to embodiments of the present invention.

The following terms used in the description that follows. The definitions are provided for clarity of understanding:

| | |
|---|---|
| assessment data - | assessment data is all data relevant to the health of a patient. |
| healthcare location - | A "healthcare location;" a facility, whether temporary or permanent, that is not generally equipped to provide expert medical care on a twenty-four basis. By way of illustration and not as a limitation, a healthcare location may be a remote clinic, a doctor's office, a field hospital, a disaster aid station, a patient transport vehicle and similar care facilities |
| caregiver - | an individual providing care to a patient. Examples include a nurse, a doctor, medical specialist (for example and without limitation an intensivist, cardiologist or other similar medical specialist). |
| clinical data - | data relating to the observed symptoms of a medical condition. |
| monitored patient - | a person admitted to a healthcare location. |
| monitored data - | data received from monitoring devices connected to a monitored patient. |
| monitored patient - | a monitored patient from whom monitored data is collected and whose condition is subject to continuous real-time assessment from a remote command center. |
| patient data - | data relating to a patient's diagnosis, prescriptions, history, condition, laboratory results and other health-relevant data. |
| perinatologic data - | data indicative of the condition of both a mother patient and a fetal patient prior to childbirth. |
| physiological data - | any data relating to the functions of the human body and its processes. |
| symptom - | any sign or indication of a health condition that can be identified from patient reports and/or assessment data. |

An embodiment of the present invention uses a telecommunications network to facilitate rules-based care of patients receiving perinatologic care in a healthcare location. In this embodiment, "patients" encompasses a pregnant woman patient (herein, the "mother patient") and the unborn fetal patient (herein, the "fetal patient").

As used herein, a healthcare location may be a hospital, a remote clinic, a doctor's office, a field hospital, a health maintenance organization, a disaster aid station, a patient transport vehicle, an emergency room, an intensive care unit, an operating room, a step down unit, a nursing home, a space-based healthcare facility, a residence, a labor delivery unit, a floor bed, and a mobile healthcare facility. By way of illustration and not as a limitation, a mobile healthcare facility may be a ship, a helicopter, and an ambulance. The patients may be selected for monitoring based on criteria established for the woman patient, the fetal patient or both.

Patient monitoring equipment acquires monitored data elements from both the mother patient and the fetal via patient monitoring station and transmits the monitoring data over a network to a remote command center. Monitored data comprises physiological data elements, video data elements, and audio data elements. The remote command center receives the monitoring data from all patient monitoring stations. The remote command center also accesses other data relating to the condition of either or both patients. By way of illustration and not as limitation, the remote command center has access to data relating to personal information about the mother patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare location. The remote command center may also have information about the fetal patient. By way of illustration and not as a limitation, the remote command center may have access to the medical history of the fetus (size, growth rate, orientation in the uterus, gender), medical history (injuries, surgeries), and laboratory results (genetic tests, blood tests, fetal heart rate records and other data elements). The data available to the remote command center over the network, that is, the monitoring data and the patient data, are collectively referred to as "assessment data."

A rules engine applies a rule or rule set to the data elements selected from the assessment data from each monitored patient to determine whether the rule for that patient has been contravened. A mother-specific rule may require monitored data of the fetal patient and the fetal patient may require monitored data of the mother patient. In the event a rule has been contravened, an alert at the remote command center is triggered. Rules for each monitored patient may be established and changed at the remote command center for each patient as the patients' conditions warrant. In one embodiment of the present invention, a rule is established to determine whether a patient's condition is deteriorating. In another embodiment, a rule is established to determine whether a patient's condition is improving. In yet another embodiment of the present invention, an alert that a rule has been contravened comprises advice on treatment of the patient.

By way of illustration and not as a limitation, assessment data for the fetus comprises the fetal heart rate of the fetal patient, the variability of the fetal heart rate, pH and all other laboratories in the parent patent (including toxicology), oxygen saturation, arterial and venous oxygen, carbon dioxide and carbon monoxide, blood pressure, age (level of prematurity), ultrasound assessment, and amniotic fluid evaluation for microbiology and all above laboratories, and the strength and frequency of contractions of the mother patient. A fetal patient rule is established to determine whether the contractions of the mother patient are causing stress in the fetal patient. In an embodiment of the present invention, the fetal heart rate is monitored externally (through the mother patient's skin) and the fetal patient rule comprises an algorithm to determine whether to monitor the fetal heart rate internally (through an electrode connected to the scalp of the fetal patient).

By way of illustration and not as a limitation, assessment data for the mother patient comprises vital signs, tochodynamometer (external uterine pressure), internal uterine pressure, ultrasound assessment, toxicology (poisons and overdoses), and airway evaluation.

In another embodiment of the present invention, a fetal patient specific rule comprises a stress algorithm that determines whether a cesarean section is appropriate. Other fetal patient rules may be applied to determine, for example but not as a limitation, cord compression (there is no free blood flow to the fetus), fetal heart block (where there is a block of electrical flow within the heart muscle causing an altered heart rhythm), fetal malposition, fetal hypoxia (insufficient oxygen supply to the fetus), infection (monitoring cannot diagnose an infection, but can suggest the presence of an infection), uteroplacental insufficiency (insufficient oxygen exchange between the uterus and the placenta), fetal distress, and abruptio placenta.

In an embodiment of the present invention, a monitored patient care system provides care to monitored patients based on the capabilities of the healthcare location. In this embodiment, the rules engine, the decision support algorithms, the order writing software facilities, and the continued care software are adapted to the capabilities of the healthcare location based on the application of site assessment rules to the healthcare location. In another embodiment of the present invention, components of a healthcare location patient care system may be supplied to the healthcare location to improve the level of its treatment capabilities. In still another embodiment of the present invention, components of the healthcare location are packaged and assigned a site assessment code. The code is used by the remote command center to predetermine elements of the site assessment process thereby simplifying that process.

FIG. 1 illustrates a block diagram of the components of a monitored patient care system according to embodiments of the present invention. A monitored patient care system 100 comprises patient monitoring station "A" 105. While FIG. 1 illustrates a single patient monitoring station, the invention is not so limited. Multiple patient monitoring stations may be used without departing from the scope of the present invention. For the sake of clarity, the description that follows will refer to patient monitoring station "A" 105. However, the description applies to all patient monitoring stations within the monitored patient care system 100.

Patient monitoring station "A" 105 comprises a general purpose computer 110, a patient monitoring device 115, a camera 120, and a duplex audio system 125. While FIG. 1 illustrates a patient monitoring device, the invention is not so limited. Multiple patient monitoring devices may be used without departing from the scope of the present invention. For the sake of clarity, the description that follows will refer to patient monitoring 115.

General purpose computer 110 provides data entry, display and printing capabilities through means known to those skilled in the art. As will be appreciated by those skilled in the art, patient monitoring device 115 may be portable without departing from the scope of the present invention. In still another embodiment, the portable monitoring station is wearable by the patient. By way of illustration an not as a limitation, the patient is a fetus carried by an expectant mother and wherein the transportable monitoring station comprises a tocodynamometer that transmits information wirelessly to the remote command center where the patient data is evaluated in an automated fashion.

In an embodiment of the present invention, monitoring station "A" 105 is integrated into a patient supporting device, as for example and not as a limitation, a bed, a gurney, wheelchair, a chair, a recliner, and a stretcher. Monitoring station "A" 105 may also be assembled on a cart or other mobile structure. In yet another embodiment of the present invention, monitoring station "A" 105 is located in an examination room.

As will be appreciated by those skilled in the art, monitoring station "A" 105 may be portable without departing from the scope of the present invention. In an embodiment of the present invention, monitoring station "A" 105 is integrated into a patient supporting device, as for example and not as a limitation, a bed, a gurney, a wheelchair, a chair, a recliner, and a stretcher. Monitoring station "A" 105 may also be assembled on a cart or other mobile structure.

The components of patient monitoring station "A" 105 are connected to network 145 via network interface 140. Network 145 may be a wired network, a wireless network, a satellite network, a public switched telephone network, an IP network, a packet switched network, a cell phone network, a cable network, and a coax network, a hybrid fiber coax network.

Pharmacological supplies 180 comprise an inventory of medicines that is provided to a healthcare location depending on circumstances. By way of illustration and not as a limitation, a monitored patient care system 100 may be operated in a full service hospital facility, a prenatal care clinic or dropped shipped to a disaster area where the primary concern is sanitation-based illnesses. In the former instance, the full service hospital would have access to all available medications. However, in the case of the drop shipped field hospital, pharmacological supplies 180 would comprise those medications, diagnostic tools, and preventive agents that are useful in countering the expected diseases and not readily available to the healthcare location. In contrast, if the disaster area is most likely to experience patients with physical injuries, pharmacological supplies would be weighted to supplies needed to diagnose, treat, and comfort the wounded.

An optional site assessment module 130 and an optional patient assessment module 135 connect to network interface 140 via general purpose computer 110. It is anticipated that a monitored patient care system 100 equipped with the optional site assessment module 130 and the optional patient assessment module 135 will be used in healthcare locations that have limited resources. Site assessment module 130 provides information indicative of the ability of a healthcare location to provide diagnostic, laboratory, surgical, and pharmacological services. In an embodiment of the present invention, the site assessment module acquires data from the healthcare location produces service level measures comprising an inventory of available monitoring data elements, an inventory of available diagnostic services, an inventory of available surgical treatment services, and an inventory of available laboratory services. These data may be acquired via a survey or by reference to a database in which the survey data of the healthcare location are stored. Alternatively, in another embodiment of the present invention, a monitored patient care system comprises an assessment code that details the capability of the monitored patient care system 100. By way of illustration and not as a limitation, the assessment code may indicate the number of monitoring devices incorporated into the monitored patient care system 100, the patient parameters that can be acquired using the monitoring devices, and the pharmacological supplies 180 provided with the monitored patient care system 100.

Optional patient assessment module 135 provides patient condition data indicative of a monitored patient to remote command center 150. In an embodiment of the present invention, patient assessment module 135 acquires data relating to a patient's diagnosis, prescriptions, history, condition, laboratory results and other health-relevant data. These data may be acquired via a survey or by reference to a database in which the patient condition data are stored.

As will appreciated by those skilled in the art, site assessment module 130 and a patient assessment module 135 may be standalone components or may be software applications operating on general purpose computer 110.

Also connected to network 145 is remote command center 150. Remote command center 150 comprises a patient rules generator 155, a rules engine 160, decision support system 155, display and control system 165, and audio/video (A/V) conferencing server 170. Decision support system 158 issues instructions to the rules generator 155 when rules required for a patient. Once the rules are generated by rules generator 155, the decision support system 158 causes the rule to be referred to the rules engine 160 for subsequent application to the specific patient for whom the rule was originally generated. A network interface 175 provides connectivity between network 145 and the other elements of the remote command center. Network 145 is configured to permit access to external networks (not illustrated), such as the Internet.

Video camera 120 is movable both horizontally and vertically and zoomable through remote commands from the display and control system 165 of remote command center 150 so that specific views of the patient may be obtained both up close and generally. Duplex audio system 125 comprises a speaker and microphone (not illustrated) to permit both one-way audio monitoring of the patient and two-way communication with the patient or others in proximity to patient monitoring station "A" 105.

Patient monitoring device 115 acquires physiological data from a patient in real-time. In an embodiment of the present invention, general purpose computer 110 comprises a printer that receives and prints orders and instructions from an authorized remote caregiver. By way of illustration and not as a limitation, an order comprises a lab order, a medication, and a procedure. Orders are tailored to the capabilities of the healthcare location patient care system 100.

A network interface 140 provides access to network 145 for transmission of the monitored data, video signal, and audio signals to the remote command center 125 and the receipt of the audio signals and, optionally, printer signals at the monitoring station.

Figure 2:
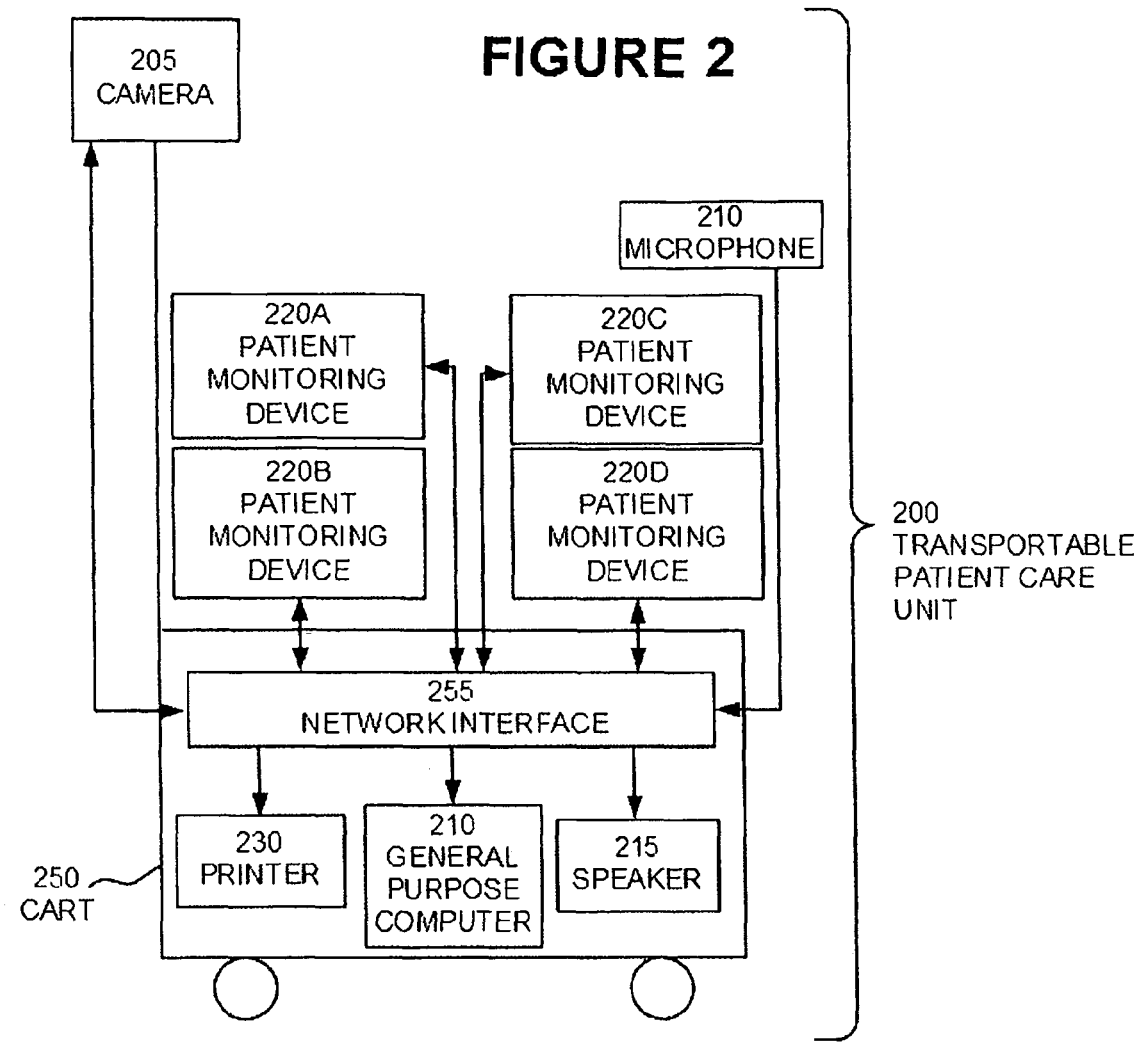
FIG. 2 illustrates the components of a transportable patient care unit according to embodiments of the present invention.

FIG. 2 illustrates the components of a transportable patient care unit according to embodiments of the present invention. A transportable patient care unit 200 comprises the components illustrated in FIG. 1 mounted on a cart 250. Video camera 205 is movable both horizontally and vertically and zoomable through remote commands from the display and control system 165 of remote command center 150 (see, FIG. 1) so that specific views of the patient may be obtained both up close and generally. A microphone 210 and a speaker 215 permit both one-way audio monitoring of the patient and two-way communication with the patient or others located in proximity to transportable patient care unit 200. Patient monitoring devices 220A-220D acquire physiological data from a patient in real-time. A printer 230 receives and print orders from an authorized caregiver. By way of illustration and not as a limitation, an order comprises a lab order, a medication, and a procedure. A network interface 255 provides access to a network (see FIG. 1, 150) for transmission of the monitored data, video signal, and audio signals to a remote command center and the receipt of the audio signals and printer signals at the monitoring station. A general purpose computer 210 allows on site care givers to provide additional data that may be germane to the care of the patient.

Referring again to FIG. 1, the remote command center 125 receives monitored data from patient monitoring station "A" 105 and patient condition data from patient assessment module 135 via network 145 through network interface 175. Monitored data comprises real-time data received from monitoring equipment at patient monitoring station "A" 105 that is configured to receive physiological data monitored patient and associated with patient monitoring station "A" 105.

The rules generator 155 and the rules engine 160 facilitate detection of impending problems and automate problem detection thereby allowing for intervention before a patient condition reaches a crisis state. Rules engine generator 155 establishes one or more rules for the monitored patient associated with patient monitoring station "A" 105. In an embodiment of the present invention, rules generator 155 generates a rule that is consistent with the patient assessment data of the mother patient and the fetal patient and with the service level measures established by the site assessment module 130. The rules engine 160 continuously applies a rule to selected data elements of patient assessment data (assessment data is all data relevant to the health of a patient) to determine whether the rule for a monitored patient has been contravened. In the event the rule has been contravened, the remote command center issues an alert. In a perinatological setting, the rules generator 155 generates rules for both the mother patient and the fetal patient. As will be appreciated by those skilled in the art, in the perinatological setting, the rules for these patients may be use the data of one patient in assessing the condition of the other patient. The rules engine 160 applies the mother rules and the fetal rules in parallel. By way of illustration and not as a limitation, a rapid fetal heart rate in the presence of a maternal fever may provoke an alert directed to the mother. However, a rapid fetal heart rate in the absence of a maternal fever or contractions may provoke an alert directed to the fetus.

In one embodiment of the present invention, a rule is established to determine whether a patient's condition is deteriorating and an alert comprises an intervention order and protocol. In another embodiment of the present invention, the rules engine determines whether a monitored patient requires monitoring by a monitoring station. If not, a release protocol and order are issued. In still another embodiment of the present invention, a rule dictates threshold limits for changes over time of specific vital sign data. Thresholds that are patient-specific disease-specific are established. The rules engine then evaluates the monitored data for the specific vital sign data to determine if a change threshold has been exceeded.

For example, a patient with coronary artery disease can develop myocardial ischemia with relatively minor increases in heart rate. Heart rate thresholds for patients with active ischemia (e.g. those with unstable angina in a coronary care unit) are set to detect an absolute heart rate of 75 beats per minute. In contrast, patients with a history of coronary artery disease in a surgical ICU have thresholds set to detect either an absolute heart rate of 95 beats per minute or a 20% increase in heart rate over the baseline. For this threshold, current heart rate, calculated each minute based on the median value over the preceding 5 minutes, is compared each minute to the baseline value (the median value over the preceding 4 hours).

In another embodiment of the present invention, a rule is based on multiple variables. By way of illustration, a rule is contravened if the rules engine determines that monitored data reflects both a simultaneous increase in heart rate of 25% and a decrease in blood pressure of 20%, occurring over a time interval of 2 hours.

For multi-variable rules, thresholds rely on known or learned associations between changes in multiple variables, which variables may comprise diverse data types. Thus, a rule may associate monitored physiological data with patient clinical data. The association may change depending on the diagnosis of the patient, the medication given the patient, and the results of laboratory data. For example, a rule may associate central venous pressure and urine output, because simultaneous decreases in these two variables can indicate that a patient is developing hypovolemia. Another rule may cause the rules engine to evaluate laboratory data (e.g. looking for need to exclude active bleeding and possibly to administer blood).

In an embodiment of the present invention, a rule established for a monitored patient and the monitored patient is associated with a particular monitoring station. In this embodiment, if the patient were later associated with a different monitoring station, the remote command center would associate the rule with the different monitoring station at the time that the association between the monitored patient and the different monitoring station is made. In this way, rules "move" with the patient without manual intervention.

In another embodiment of the present invention, patient rules generator 155 establishes one or more rules for the monitored patient associated with patient monitoring station "A" 105. The patient rules generator 155 receives rules performance measures indicative of the ability of the rule to predict changes in the condition of a patient and uses these measures to assess the efficacy of the rule. By way of illustration and not as a limitation, the rules performance measures may be derived from survey data from healthcare professionals with experience with the rule or with the relationship of certain variables used by the rule to other variables or to a particular medical condition. Alternatively or in conjunction with survey data, the patient rules generator 155 may review historical data using multivariate analyses to relate variables, rules, and patient outcomes. By way of illustration and not as a limitation, the patient rules generator 155 may use ANOVA or BSS to automatically produce rules performance measures of existing rules and to identify new relationships among variables that may be used to form new rules. The patient rules generator 155 may update a rule, determine that a rule is acceptable as is, or determine that there is insufficient data to revise a rule.

The patient rules generator 155 may also evaluate the assessment data of patients with similar conditions to determine whether a predictive rule can be written and applied to patients with the same or similar conditions. The rules generator 155 may also test a proposed rule against historical data to determine whether the rule is predictive of a change in a patient's condition.

In yet another embodiment of the present invention, the patient rules generator 155 generates a rule that is consistent with the service level measures established by a site assessment module 130.

In another embodiment of the present invention, patient monitoring equipment acquires monitored data elements from a patient monitoring station and stores monitoring data in general purpose computer 110. The stored monitoring data is sent from general purpose computer 110 to the remote command center 150 along with patient data under control of an optional communications scheduler 112 at a pre-established time such as hour or when an "event" occurs as noted below, or when requested by remote command center 150. The remote command center 150 evaluates the "delayed" monitored data and assessment data in the same manner as if these data were received in real time. By way of illustration, the remote command center will generate rules using patient rules generator 155, apply those rules using rules engine 160 to the delayed monitored data and patient data and provide guidance to the monitored patient care system 100. The decision support algorithms of decision support system 158 may also be applied to the delayed monitored data and patient data. This embodiment of the present invention thus provides high quality care in environments where continuous high bandwidth communications are not available or economically infeasible.

In still another embodiment of the present invention, the delivery of stored monitoring data and patient data is expedited by an urgent consultation warning system (herein, the UCWS) operated by general purpose computer 110. The UCWS constantly evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the remote command center 150 for evaluation.

Figure 3:
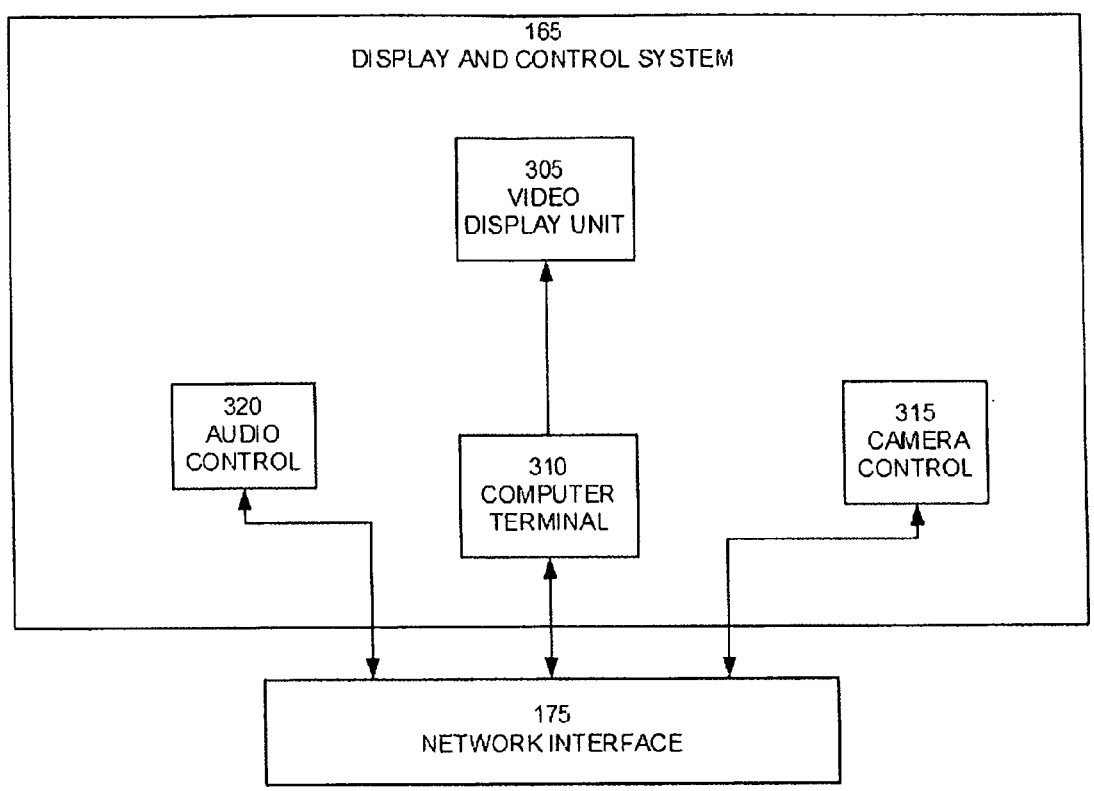
FIG. 3 illustrates a display and control system according to an embodiment of the present invention.

Referring to FIG. 1, the display and control system 165 provides the human interface for the remote command center. FIG. 3 illustrates a display and control system according to an embodiment of the present invention. A display and control system 165 comprises a video display unit 305, a computer terminal 310, a camera control 315, and an audio control 320. The video display unit 305 displays real-time monitoring data and video images from patient monitoring station "A" 105. The computer terminal 310 allows selecting the layout and content displayed on the video display unit 305, provides access to the record of the patient associated with patient monitoring station "A" 105, and permits entry of data into that record. The camera control 315 permits control from the remote command center 125 of the video camera 120 (see FIG. 1) at the patient monitoring station "A" 105. The audio control permits control from the remote command center 150 of a microphone and a speaker within the duplex audio system 125 of patient monitoring station "A" 105. Connectivity between the components of the display and control systems 165 and patient monitoring station "A" 105 is provided by network interface 175, network 145, and network interface 140.

Figure 4:
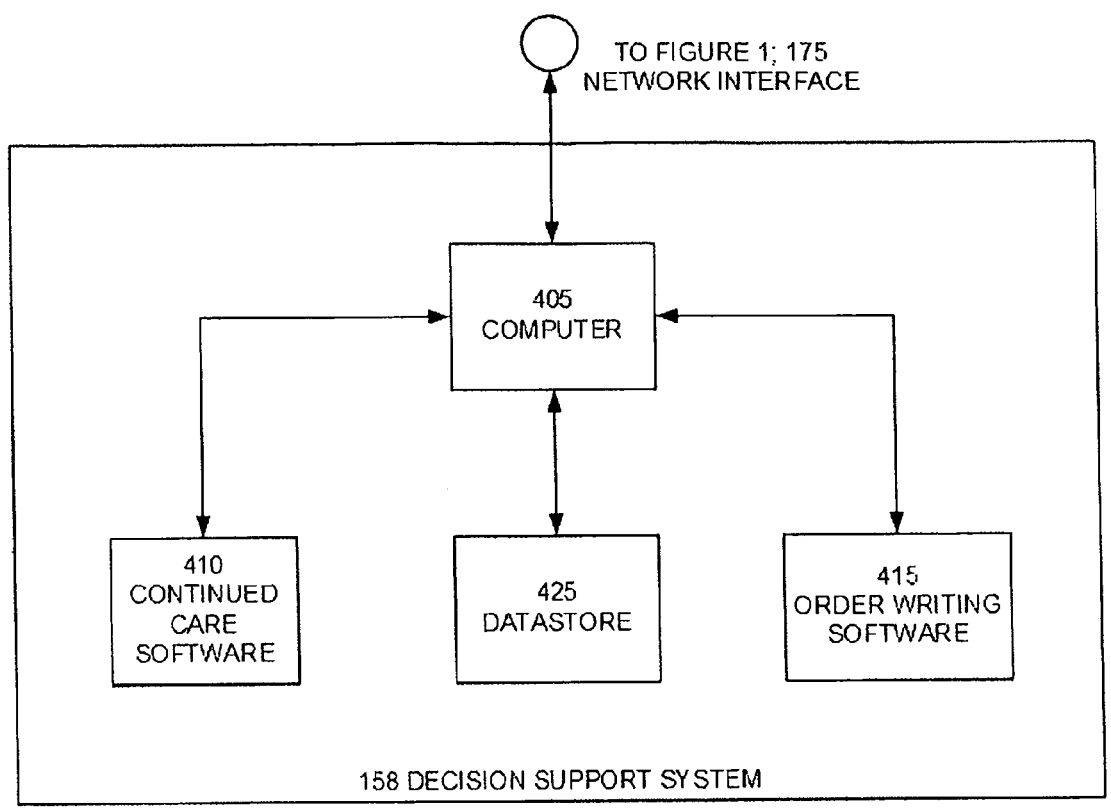
FIG. 4 illustrates a decision support system according to an embodiment of the present invention.

Referring again to FIG. 1, the remote command center 150 comprises decision support system 158. FIG. 4 illustrates a decision support system according to an embodiment of the present invention. Referring to FIG. 4, decision support system 158 is connected to network interface 175 and comprises a computer 405. Computer 405 operates continued care software 420 and order writing software 415. Continued care software 410 and order writing software 415 make calls to datastore 425 to access the assessment data related to a particular monitored patient associated with patient monitoring station "A" 105 (see, FIG. 1).

Continued care software 420 comprises decision support algorithms that operate on elements of assessment data and/or input from a caregiver to facilitate decisions relating to diagnosis, treatment and triage. Continued care software may be applied at the time the patient is admitted and throughout the patient's stay within a treatment facility. Thus, a diagnosis may be made based on the initial data acquired during admission, following the completion of laboratory procedures, or after other pertinent information is acquired. In an embodiment of the present invention, continued care software 420 evaluates selected data elements of assessment data continuously and provides an alert if those data are indicative of a different diagnosis. The alert may take the form of suggested diagnoses that are vetted by a series of questions posed by the continued care software 420 to a caregiver. Based on the responses to the questions, a suggested diagnosis may be eliminated. The alert may also comprise instructions for specific tests to be run on the monitored patient to help formulate a new diagnosis. Once a diagnosis is confirmed, the continued care software 420 continues to monitor changes in patient data and issues an alert if the current diagnosis should be reevaluated by a caregiver.

Decision support system 158 also issues instructions to the rules generator 155 when rules are required for a patient. Once the rules are generated by rules generator 155, the decision support system 158 causes the rule to be referred to the rules engine 160 for subsequent application to the specific patient for whom the rule was originally generated.

In another embodiment of the present invention, patient monitoring equipment acquires monitored data elements from a patient monitoring station and stores monitoring data in general purpose computer 110. The stored monitoring data is sent from general purpose computer 110 to the remote command center 150 along with patient data under control of an optional communications scheduler 112 at a pre-established time such as hour or when an "event" occurs as noted below, or when requested by remote command center 150. The continued care decision support system 158 evaluates selected data elements of the assessment data in the same manner as if these data were received in real time and provides an alert if those data are indicative of a different diagnosis.

In still another embodiment of the present invention, the delivery of stored monitoring data and patient data is expedited by an urgent consultation warning system (herein, the UCWS) operated by general purpose computer 110. The UCWS constantly evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the decision support system 158 for evaluation.

In still another embodiment of the present invention, continued care software 420 operates on a diagnosis to "triage" a patient. For example and without limitation a caregiver requests an Apache II score based on the diagnosis. Continued care software 420 calls selected data elements from datastore 425 appropriate to the diagnosis. The values of the selected data elements are weighted according to an algorithm and a patient severity score is determined. This patient severity score is used to determine whether the patient is treated in a patient monitoring station. For example, if one embodiment of the present invention, if the severity score is greater than or equal to a particular threshold, the patient is identified as requiring observation via a patient monitoring station. If the severity score is less than that threshold, the patient is triaged to a facility other than a patient monitoring station, thereby assigning patient monitoring stations to patients who are most likely to benefit from monitoring and continued assessment.

Other scoring algorithms may be used without departing from the scope of the present invention. By way of illustration and not as a limitation, continued care software 420 may comprise algorithms to perform APACHE II, APACHE III, a history of present illness (HPI) score, a review of systems (ROS) score, a past, family, and/or social history (PFSH) score, SOFA (Sequential Organ Failure Assessment) score, and a mortality prediction model (MPM) score. The scoring results from one or more of these algorithms may be used to determine a treatment plan for the patient. As will be appreciated by those skilled in the art, a scoring result may be used to determine to apply resources to a patient that is determined to be a candidate for treatment consistent with the patient's medical condition or to withhold or discontinue the application of resources to a patient that is determined to be untreatable consistent with standards of medical ethics.

In yet another embodiment of the present invention, a patient is scored continuously based on patient assessment data that is accessed by the continued care software 420. A scoring algorithm or a collection of algorithms are applied to updated assessment data to determine whether the current treatment plan is viable or should be amended.

In another embodiment of the present invention, computer 405 operates order writing software 415, either independently or in conjunction with the operation of continued care software 420 to order tests to complete the data required for a potential diagnosis.

According to another embodiment of the present invention, the orders issued by order writing software 415 are consistent with the service level measures established by the site assessment module 130.

Figure 5:
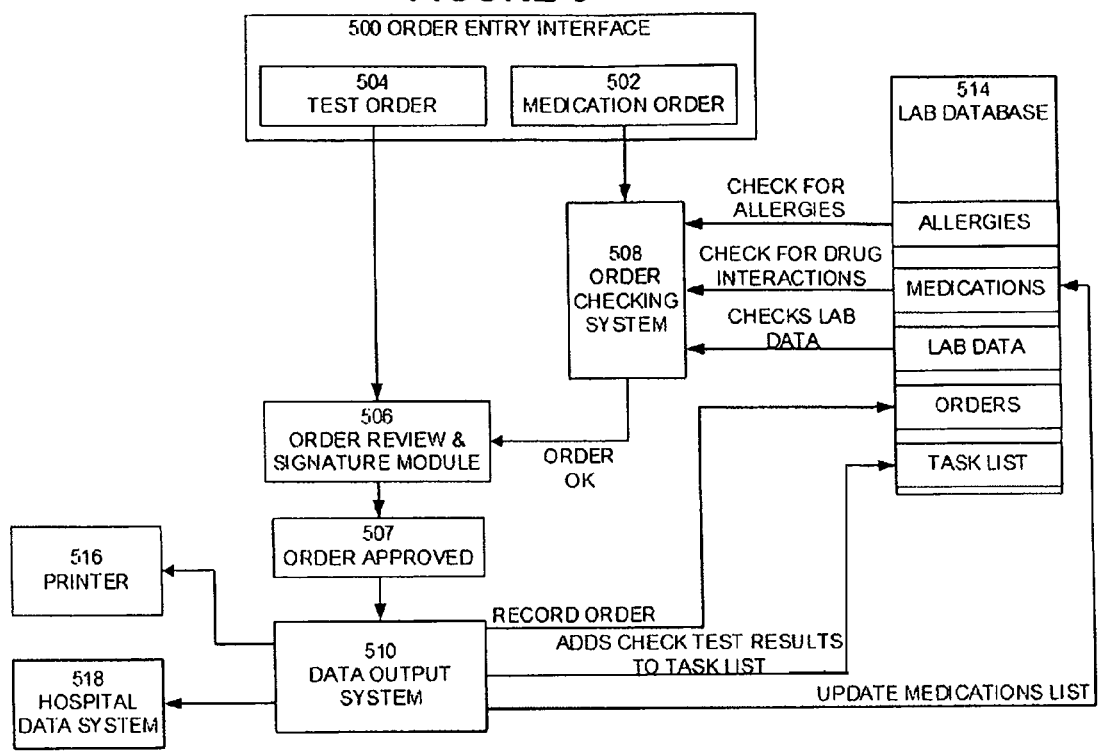
FIG. 5 illustrates an order writing data flow according to an embodiment of the present invention.

FIG. 5 illustrates an order writing data flow according to an embodiment of the present invention. Referring to FIG. 5, order entry user interface 500 allows the caregiver to order procedures and medication to assist the patients at a patient monitoring station. For example, the caregiver can order an ECG 504. Thereafter the order is reviewed and a digital signature relating to the caregiver is supplied 506. Once reviewed and signed off, the order is approved 507 and sent to the data output system 510. Thereafter the data output system prints the order to the printer at a patient monitoring station 516. For record keeping purposes the order is exported in the HL7 language to the hospital data system 518. In addition the data output system adds an item to the database that will subsequently cause a caregiver to check the ECG results. This notification to the task list is provided to the database 514. In addition, as part of the database an orders file relating to the specific patient is also kept. The fact that an ECG has been ordered is entered in the orders file for that patient.

The order entry functionality of the present invention provides a critical service for obtaining information on the patient during admission, medical orders, and procedures provided to the patient during the ICU stay. For example:

| | |
|---|---|
| Radiology: | Contains all radiology performed on a particular patient. |
| Radiology results: | Contains the results of each radiology test performed on the particular patient. |
| Drugs: | Contains all relevant information for all the drugs that a patient has been administered. |
| Laboratory: | Contains all laboratory tests ordered for a patient. |
| Microbiology result: | Contains the results of microbiology organisms taken on a patient. |
| Laboratory result: | Contains the results for a laboratory test ordered for a particular patient. |

In a similar fashion using the order entry user interface 500 the caregiver can order medications 502 for a patient.

According to an embodiment of the present invention, the order entry interface 500 uses an identification algorithm to facilitate order entry. As text is entered into the interface, suggested entry values are provided to the user for selection, thereby reducing the entry time and the opportunity of mistakes.

The medication order then is provided to an order checking system 508. The order checking system retrieves information from the database 514 relating to allergies of the patient and medication list that comprises medications that are already being administered to the patient. This allows for the order checking system to check for drug allergies and drug interactions. Further laboratory data is extracted from the database 514 and the order checking system checks to insure that there will be no adverse impact of the recommended dosage upon the renal function of the patient. Additionally, a patient with kidney and/or liver problems may have the dosage adjusted based on the slower excretion time for such patients. Once the order checking system 508 is completed, the order is approved and provided to the order review and signature module 506. In this module the digital signature of a caregiver is affixed to the order electronically and the order is approved 507. Thereafter it is provided to the data output system 510 where again the orders are printed or transmitted via HL7 for the patient monitoring station 516, for the pharmacy 517 and for the treatment facility data system 518. In this case, any medications that are ordered are then provided to the medications list file in the database 514 so that the complete list of all medications that are being administered to the patient is current.

In an embodiment of the present invention, order checking system 508 determines whether the order is consistent with the service level measures established by the site assessment module 130. If the order is not consistent with the service level measures, the order is suppressed and the caregiver is notified that an alternative treatment is required.

As noted, the order writing software 415 may also interact with continued care software 410. Referring again to FIG. 4, a caregiver selects a suggested diagnosis from the continued care software 420 and enters the order writing software 415. As previously described, the orders issued by order writing software 415 are consistent with the service level measures established by the site assessment module 130. The order writing software identifies the appropriate test or tests and issues the actual order or orders for the identified tests. Each order is then sent to the appropriate testing facility. The tests are conducted, and the completion of the order is reported to the data store 425 and the completion information is received by the order writing software 415. Additionally, continued care software 420 acquires the test results from the datastore 425 and updates the list of suggested diagnoses.

Continued care software 420 provides reference material directed to the standardized treatment of the monitored patient. In order to standardize treatment provided to monitored patients at the highest possible level, decision support algorithms are used in the present invention. These include textural material describing the topic, scientific treatments and possible complications. This information is available in real time to assist in all types of clinical decisions from diagnosis to treatment to triage.

In an embodiment of the present invention, the decision response algorithms are responsive to the service level measures established by the site assessment module 130. In this embodiment, the algorithms adjust the response to fit the capabilities of the healthcare location.

As noted earlier, an aspect of the present invention is to standardize care and treatment across patient monitoring stations. This is effective in the present invention by providing decision support to caregivers as well as information concerning the latest care and practice standards for any given condition. Table 1 below is an exemplary list of a wide variety of conditions within the general categories of cardiovascular, endocrinology, general, gastrointestinal, hematology, infectious diseases, neurology, pharmacology, pulmonary, renal, surgery, toxicology, for which algorithms of care have been developed. As will be appreciated by those skilled in the art, the list in Table 1 is not exhaustive and other decision support algorithms may be developed for other conditions without departing from the scope of the present invention.

TABLE 1

Figure 6A:
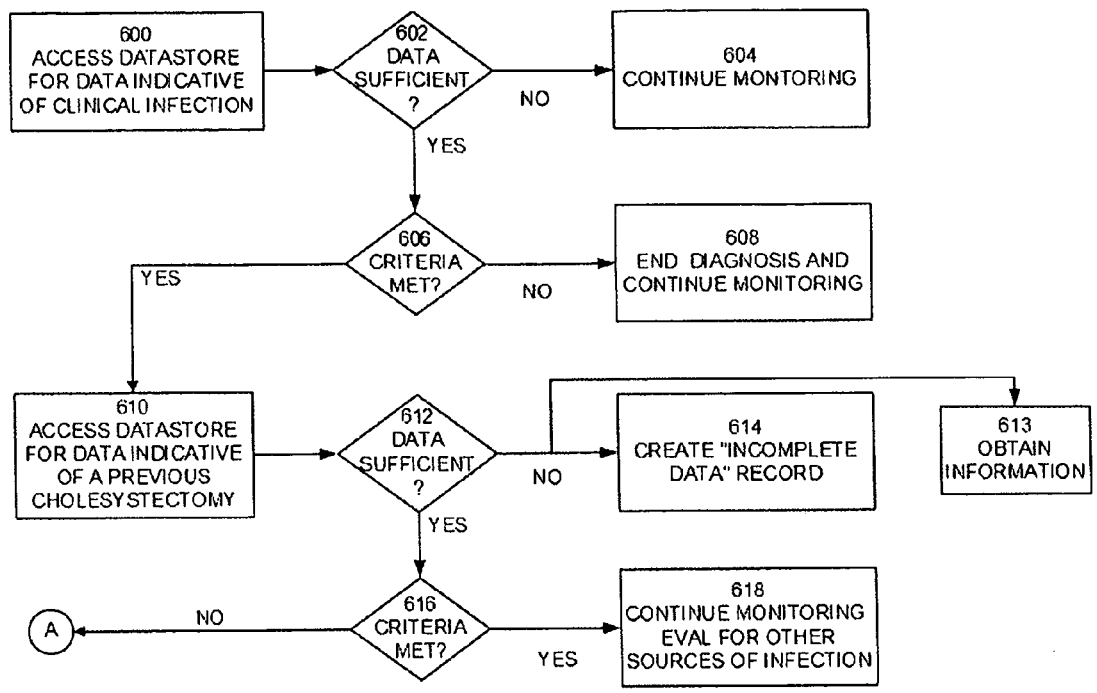
FIGS. 6A, B, C, and 6D illustrate the flow of a decision support algorithm for acalculous cholecsystitis according to an embodiment of the present invention.

Bradyarrhythmias diagnosis & treatment
Cardiogenic shock treatment
Cardio-pulmonary resuscitation treatment
Congestive heart failure diagnosis & treatment
Emergency cardiac pacing indications
Fluid resuscitation indications & treatment
Hypertensive crisis treatment
Implantable cardio-defibrillators indications
Magnesium treatment
Treatment of hypotension
Myocardial infarction diagnosis & treatment
Pulmonary artery catheter indications
Pulmonary embolism diagnosis
Pulmonary embolism treatment
Supra-ventricular tachyarrhythmias diagnosis & treatments
Venous thromboembolism prophylaxis treatment
Venous thrombosis: diagnosis & treatment
Ventricular arrhythmias diagnosis & treatment
Diabetic ketoacidosis diagnosis and treatment
Hyperglycemia: insulin treatment
Thyroid disease diagnosis and treatment
Hepatic failure diagnosis and treatment
Upper gastro-intestinal bleeding: stress prophylaxis treatment
Heparin treatment
Heparin-induced thrombocytopenia diagnosis and treatment
The bleeding patient diagnosis and treatment
Thrombocytopenia diagnosis and treatment
Transfusion indications
Bloodstream infections diagnosis and treatment
Candiduria diagnosis and treatment
Endocarditis diagnosis and treatment
Fever of Unknown Origin diagnosis
HIV+ patient infections diagnosis and treatment
Non-infectious causes of fever diagnosis
Septic shock diagnosis and treatment
Agitation, anxiety, depression & withdrawal treatment
Myasthenia gravis diagnosis and treatment
Aminoglycoside dosing and therapeutic monitoring
Analgesia treatment
Penicillin allergy diagnosis and treatment
Adult Respiratory Distress Syndrome: hemodynamic treatment
Adult Respiratory Distress Syndrome: steroid treatment
Adult Respiratory Distress Syndrome: ventilator treatment
Asthma diagnosis & treatment
Bronchodilator use in ventilator patients
Chest X-ray indications
Noninvasive modes of ventilation indications
Endotracheal tubes & tracheotomy indications
Ventilator weaning
Hyperkalemia: diagnosis & treatment
Hypernatremia: diagnosis & treatment TABLE 1-continued Hypokalemia: diagnosis & treatment
Hyponatremia: diagnosis & treatment
Oliguria diagnosis and treatment
Obstetrical complications and treatment
Diagnosis and treatment of post-operative bleeding
Wound healing treatment
Diagnosis and treatment of cocaine toxicity
Diagnosis and treatment of alcohol withdrawal
Diagnosis and treatment of latex allergy
Deep Venous Thrombosis prophylaxis treatments
Acid-base disturbance diagnosis and treatment
Electrolyte disturbance diagnosis and treatment
Viral infection diagnosis and treatment FIGS. 6A, B, C and 6D illustrate an application of a decision support algorithm for the diagnosis and treatment of acalculous cholecystitis to patient data according to an embodiment of the present invention. FIGS. 6A through 6D are exemplary only and are not limiting. As will be appreciated by those skilled in the art, decision support algorithms (DSAs) for other conditions may be implemented in the continued patient care software without departing from the scope of the present invention.

Referring to FIG. 6A, a datastore comprising patient data is accessed by the DSA 600 for data indicative of clinical infection. A determination is made whether the data is sufficient to determine whether the patient is clinically infected 602. If the data necessary to make the decision are not available, the system continues its monitoring 604 until data in the datastore indicates otherwise. Alternatively, an alert may be issued on a monitor at the command center although this is not a requirement for further tests to be ordered. Test that are ordered by the DSA are then performed on the patient to obtain the data required for the decision.

If the data are sufficient, a determination is made whether the patient meets criteria for a clinical infection as measured by elevated temperature and leukocystosis 606. In an embodiment of the present invention, the criteria are temperature great than 102 F, or a white blood cell count greater than 12,000. If the criteria for clinical infection are not met the system of the present invention goes back into its continuous monitoring mode 608. The process is then complete and the continuous monitoring of the present invention continues.

If the patient is clinically infected 606, the DSA accesses the patient data datastore and acquires data indicative of whether the patient has had a previous cholecystectomy 610. A determination is then made whether the data is sufficient to determine whether the patient has had a previous cholecsystectomy 612. If the data necessary to make the decision are not available, the DSA prompts the caregiver to find out this information 613. When the information is obtained it is put into the datastore. Notations of "incomplete data" are kept by the system so that treatment records and need for tests can be audited. This is accomplished by storing an "incomplete data" record 614.

If the data are sufficient, a determination is made whether the patient has had a previous cholecystectomy 616. If the patient has had a previous cholecystectomy, it is very unlikely that the patient has acalculous cholecystitis. Therefore the DSA has completed its analysis for acalculous cholecytitis and the continuous monitoring of the present invention continues for other possible etiologies of infection 618.

Figure 6B:
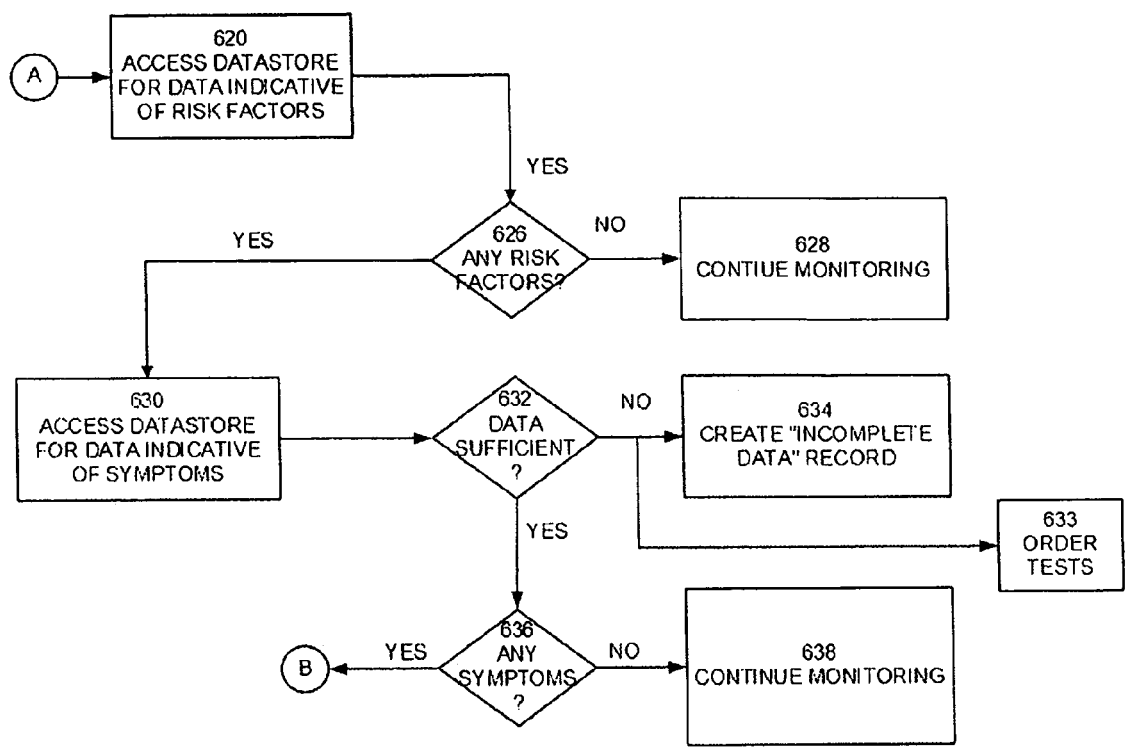

Referring to FIG. 6B, if the patient has not had a previous cholecystectomy, the DSA accesses the patient datastore and acquires data indicative of whether the patient has any of a set of risk factors 620. In another embodiment of the present invention, the risk factors comprise: 1) Prolonged intensive care unit (ICU) stay (defined as greater than six (6) days); 2) recent surgery within the last two weeks (particularly aortic cross clamp procedures); 3) hypotension (BP less than 90 mmHg); 4) positive end-expiratory pressure (PEEP) greater than ten (10) centimeters (cm); 5) transfusion greater than six (6) units of blood; 6) inability to use the gastrointestinal (GI) tract for nutrition; or 7) immunosuppression (AIDS, transplantation, or leukemia).

If the data are sufficient, a determination is made whether the patient has any of the risk factors 626. If the patient does not have any of the risk factors, the diagnostic process is then complete and the continuous monitoring of the present invention continues 628.

If the patient has any of the seven risk factors, the DSA accesses the patient data datastore and acquires data indicative of whether the patient has any of a set of symptoms 630 or abnormal laboratory values. A determination is made whether the data is sufficient to determine whether the patient has any of the symptoms 632 or abnormal laboratory values. If the data necessary to make the decision are not available, the DSA directs the order writing software 415 (see FIG. 4) to order the tests 633. Results are sent to the datastore. Notations of "incomplete data" are kept by the system so that treatment records and need for tests can be audited. This is accomplished by storing an "incomplete data" record 634. Alternatively, an alert may be issued on a monitor at the command center to check for right upper quadrant tenderness although this is not a requirement for further tests to be ordered. In another embodiment of the present invention, the symptoms comprise: right upper quadrant (RUQ) tenderness and the abnormal laboratory results comprising elevated alkaline phosphatase; elevated bilirubin; or elevated liver transaminases.

If the data are sufficient, a determination is made whether the patient has any of the symptoms 636 or abnormal laboratory values. If the patient does not have any of the symptoms or abnormal laboratory values, the DSA concludes that it is very unlikely that the patient has acalculous cholecystitis. The process is then complete and the continuous monitoring of the present invention continues 638.

Figure 6C:
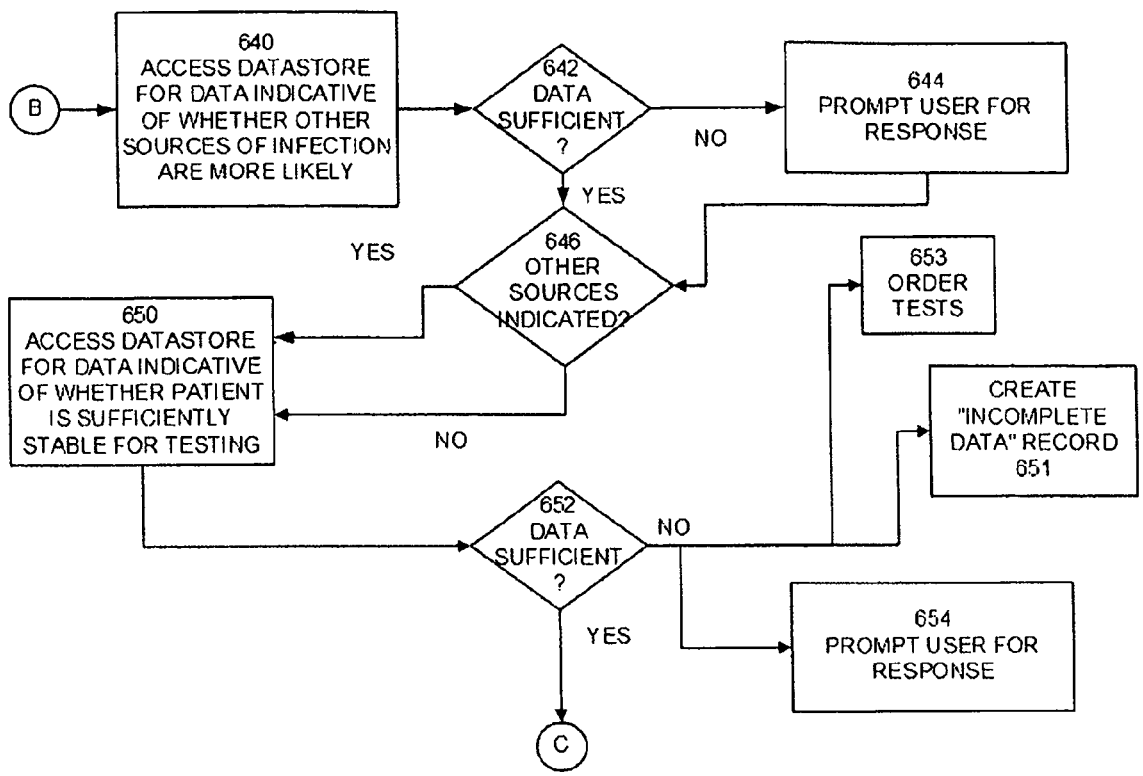

Referring to FIG. 6C, if the patient has any of the symptoms or abnormal laboratory values, the DSA accesses the patient data datastore and acquires data indicative of whether alternative intra-abdominal infectious sources are more likely 640. A determination is made whether the data is sufficient to determine whether the other infectious sources are more likely 642. If the data necessary to make the decision are not available, the DSA prompts the user for a response as to whether other infectious causes are present and considered more likely 644. The user can then provide the requested information that can be considered by the system 646 for further analysis.

If the data are sufficient, a determination is made whether other sources of infection are more likely 646. Regardless of the outcome of this determination, the DSA accesses the patient datastore and acquires data indicative of whether the patient is sufficiently stable to be subjected to testing outside of the critical care environment 650. A determination is made whether the data are sufficient to determine whether the patient is stable to go outside of the critical care environment 652. If the data necessary to make the decision are not available, the DSA prompts the user for a response 654 and may direct the order writing software 415 (see FIG. 4) to order tests or procedures 653 that will assist in such a determination. An "incomplete data" record is also created 651. Test results are sent to the datastore. Notations of "incomplete data" are kept by the system so that treatment records and need for tests can be audited. This is accomplished by storing an "incomplete data" record 654. Alternatively, an alert may be issued on a monitor at the command center although this is not a requirement for further tests to be ordered.

Figure 6D:
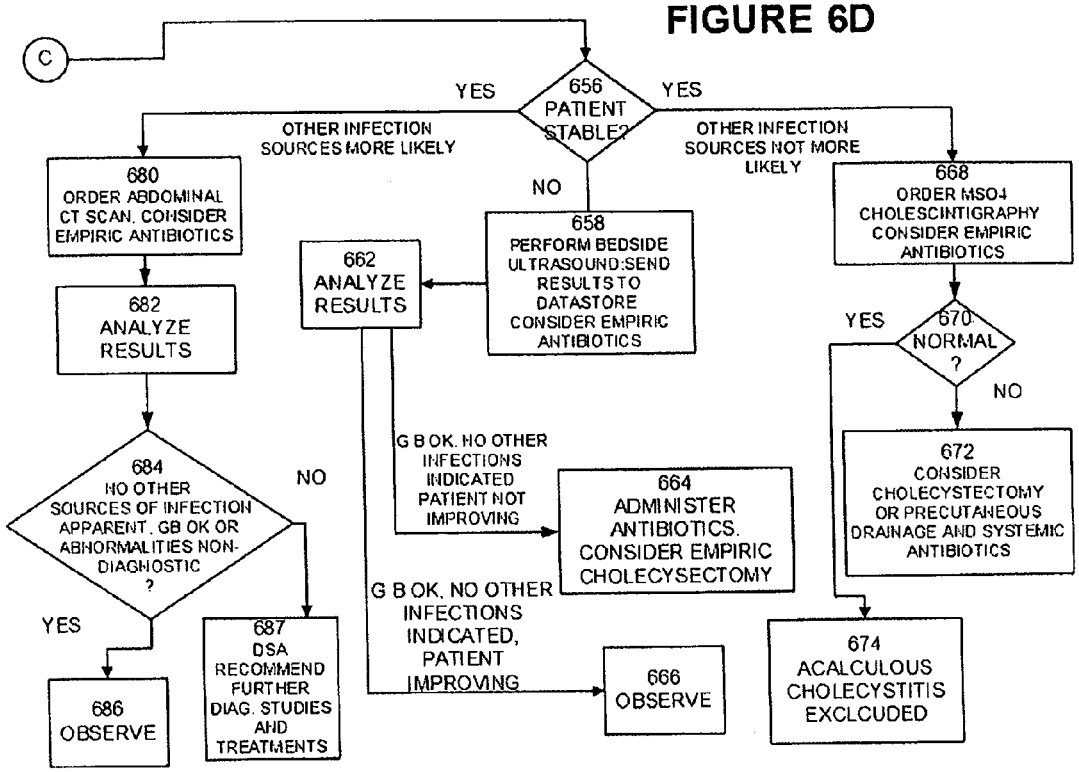

Referring to FIG. 6D, if the data are sufficient, a determination is made whether the patient is sufficiently stable to be subjected to testing outside of the critical care environment 656.

If the patient is not sufficiently stable to be subjected to testing outside of the critical care environment (regardless of whether other sources of infection are indicated), the DSA issues a message comprising a recommendation that empiric antibiotic be considered and a bedside ultrasound be performed and the results communicated to the patient datastore 658. In still another embodiment of the present invention, the DSA directs the order writing software (see FIG. 4) to order the bedside ultrasound. The DSA accesses the test results and other patient data 662. If no other infectious etiologies are identified, no abnormalities of the gall-bladder are noted, and the patient is not improving, the DSA issues a message comprising a "provisional diagnosis of acalculous cholecystitis" and recommends an empiric cholecystectomy and systemic antibiotics 664. If no other infectious etiologies are identified, no abnormalities of the gall bladder are noted, and the patient is improving, the DSA issues a message comprising a recommendation to observe the patient 666.

If the patient is sufficiently stable to go outside of the critical care environment for a test and a determination was made that no other sources of infection were indicated (see FIG. 6C, 646), the DSA issues an order that empiric antibiotics be considered and a morphine sulfate Cholescintigraphy test be performed 668 and the results communicated to the datastore. In still another embodiment of the present invention, the DSA directs the order writing software 415 (see FIG. 4) to order the test.

A determination is made whether the results of the tests are normal 670. If the test indicates an abnormality, the DSA issues a message comprising a recommendation to consider a diagnosis of acalculous cholecystitis, administer systemic antibiotics and perform either a cholecystectomy or a percutaneous drainage 672. If the results are normal, acalculous cholecystitis is excluded 674. The process is then complete and the continuous monitoring of the present invention continues.

If the patient is sufficiently stable to go outside of the critical care environment for a test and a determination was made that other sources of infection were indicated (see FIG. 6C, 646), the DSA issues an order to consider empiric antibiotics and for an abdominal CT scan to be performed 680 and the results communicated to the datastore. In still another embodiment of the present invention, the DSA directs the order writing software 415 (see FIG. 4) to order the test.

The test results and other data are analyzed 682 and a determination is made whether other infection sources are indicated and whether the gall bladder is normal or if abnormalities are present that are not diagnostic 684. If other infectious etiologies are not apparent and the test: a) demonstrates abnormalities of the gall bladder but not diagnostic; or b) no gall-bladder abnormalities are noted, the DSA issues a report comprising a recommendation to maintain continued observation of the patient 686. The process is then complete and the continuous monitoring of the present invention continues. Alternatively, if other infectious etiologies are apparent, the DSA will make recommendations as to further diagnostics and treatments.

While the decision support algorithm described with reference to FIGS. 6A, B, C and 6D refers to a continuous monitoring "mode" of the present invention, this is not meant as a limitation. As previously described, embodiments of the present invention anticipate environments in which data is stored and evaluated on a "delayed" basis. The decision support algorithms described with reference to FIGS. 6A, B, C and 6D may operate with delayed data without departing from the scope of the present invention.

In an embodiment, the fetal heart rate (FHR) is evaluated against other data relating to the mother patient and the fetal patient and interpreted as reassuring, non-reassuring, or ominous. Reassuring patterns correlate to a good fetal outcome while non-reassuring patterns do not. An ominous pattern suggests immediate delivery of the fetus.

Table 2 presents examples of non-reassuring and ominous patterns. However, the patterns identified in Table 2 are illustrative only and not meant to be limiting:

TABLE 2

| Non-Reassuring FHR Patterns | Ominous FHR Patterns |
| --- | --- |
| Fetal tachycardia | Persistent late decelerations with loss of beat-to-beat variability |
| Fetal bradycardia | Non-reassuring variable decelerations associated with loss of beat-to-beat variability |
| Saltatory variability | Prolonged sever bradycardia |
| Variable decelerations associated with a non-reassuring pattern | Sinusoidal pattern |
| Late decelerations with preserved beat-to-beat variability | Confirmed loss of beat-to-beat variability not associated with fetal quiescence, medications or severe prematurity |

FIGS. 7A, 7B, 7C, 7D, and 7E illustrate an application of a decision support algorithm for fetal well-being to patient data according to an embodiment.

Referring to FIG. 7A, a datastore comprising patient data is accessed to obtain data indicative of a baseline fetal heart rate (FHR) 700. In an embodiment, a baseline FHR is the mean FHR rounded to 5 beats per minute (bpm) during a ten minute segment, excluding periodic changes, periods of marked variability, and segments varying by more than 25 bpm. A determination is made whether the data is sufficient to determine the baseline FHR 702. If the data necessary to make the decision are not available, the reason for unavailability of data is determined 704 and orders issued to obtain the necessary data 706, 708. If the data have not been obtained from the patient, an order for a FHR may be issued. If however, the baseline FHR is not available because it could not be obtained during an FHR test, ultrasound of the mother is considered.

If the data are sufficient, the baseline FHR data are evaluated against three criteria: 710 whether the baseline FHR is in the range of 110-160 bpm; 712 whether the baseline FHR is greater than 160 bpm for longer than ten minutes; and 714 whether the baseline FHR is less than 110 bpm for 10 minutes or more.

Figure 7B:
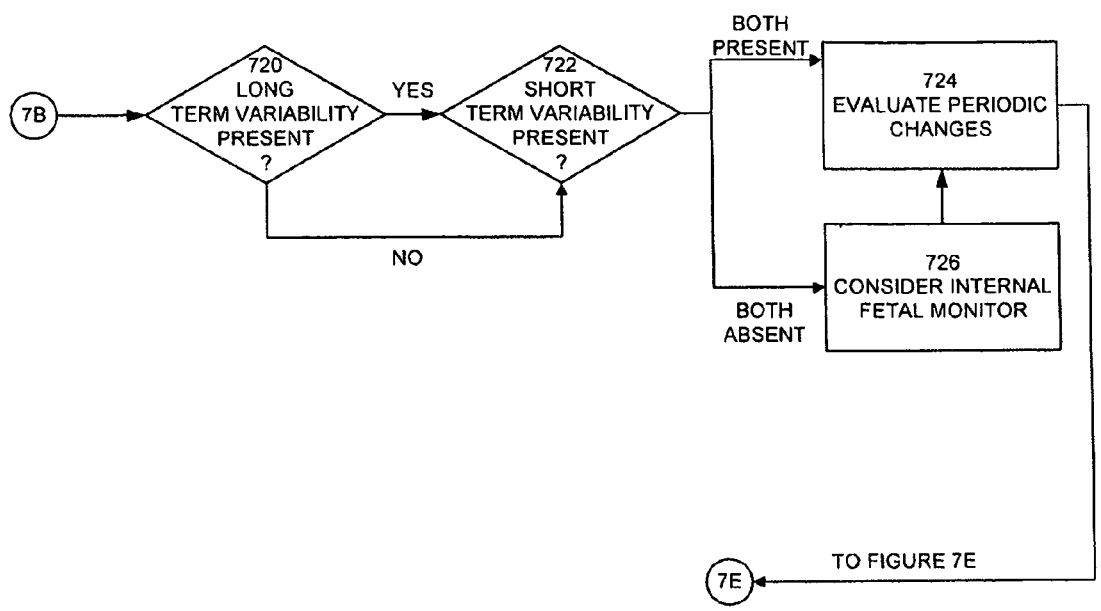

Referring to FIGS. 7A and 7B, if the baseline FHR is in the range of 110-160 bpm 710, the presence of long term variability in the FHR is evaluated at 720. In an embodiment, long term variability is characterized by a fluctuation in the baseline rate over a period of greater than two minutes and is marked by irregular amplitude and/or irregular frequency. The presence of short term variability, or beat-to-beat variability, in the FHR is evaluated at 722. If both are present, the periodic changes of the FHR are evaluated 724 in accordance with a protocol (see, 770, FIG. 7E). If both are absent, an internal fetal monitor is considered 726 and the FHR is evaluated in accordance with a protocol (see, 770, FIG. 7E).

Figure 7C:
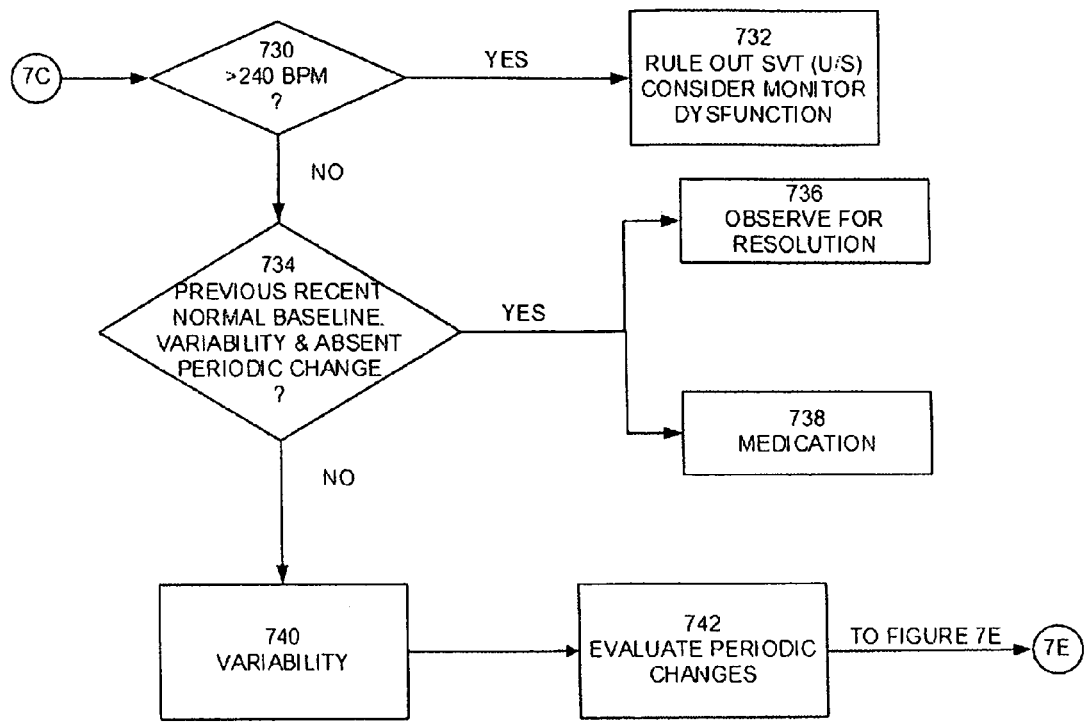

Referring to FIGS. 7A and 7C, if the baseline FHR is greater than 160 bpm for longer than ten minutes 712, a determination is made whether the FHR exceeds 240 bpm 730. If the FHR exceeds 240 bpm for ten minutes, the patient data are evaluated to rule out supraventricular tachycardia (SVT) 732. SVT is a rapid rhythm of the heart that begins in the upper chambers. The presence of SVT may be determined using ultrasound. If SVT is eliminated as a cause, the FHR monitor should be evaluated to determine whether it is working properly.

If the baseline FHR is less than 240 bpm, then the patient data are evaluated to determine whether previous baseline FHRs have been within the range of 110-160 bpm with short term and long term variability present and without periodic change 734. If previous basline FHRs meet these criteria, then the patient is observed to determine to rule out possible causes 736 and/or administer medication 738. By way of illustration and not as a limitation, causes to be consider are maternal and fetal fever and infections such as chorioamnionitis. If variability is present 740, the periodic changes are evaluated 742.

Figure 7D:
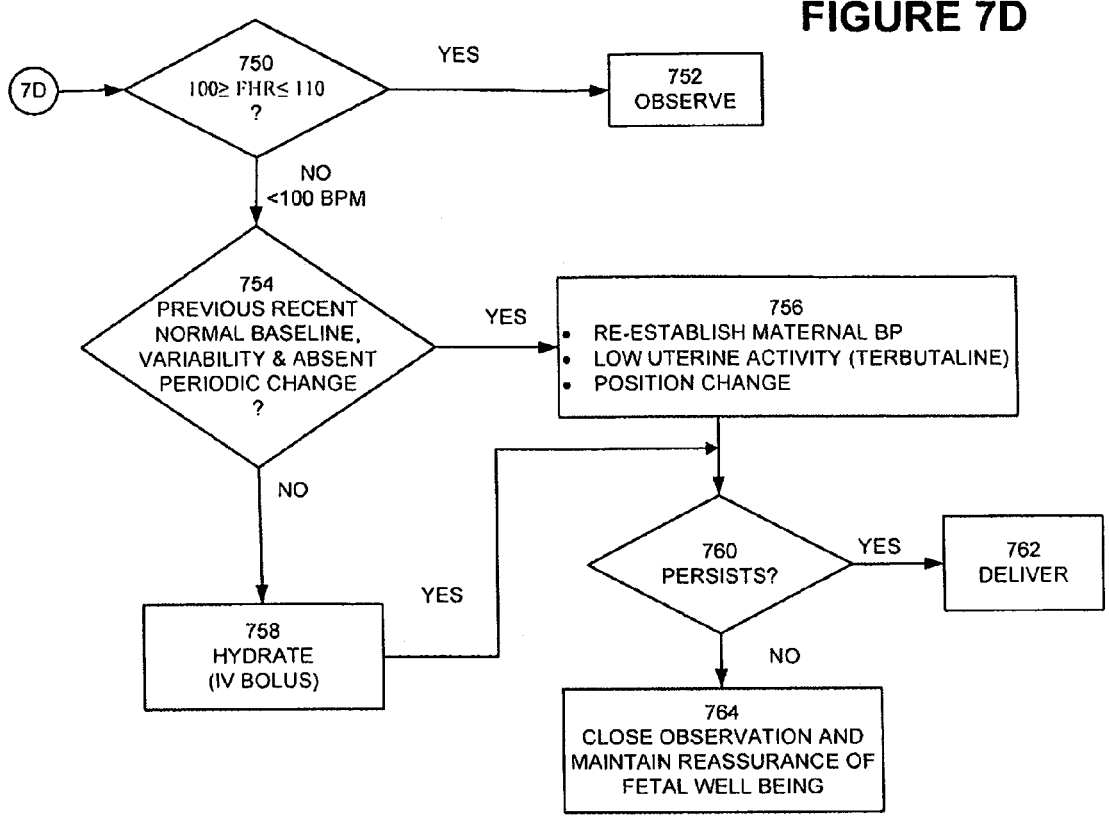

Referring to FIGS. 7A and 7D, if the baseline FHR is less than 110 bpm for 10 minutes or more 714, a determination is made whether the baseline FHR is in the range for from 100 bpm to 110 bpm 750. If the baseline FHR is within this range, the patient is observed 752. If the baseline FHR is less than 100 bpm, data indicative of the previous recent baseline are acquired from the datastore 754 and evaluated to determine whether the previous recent baseline FHR was in the "normal" range with normal variability and absent periodic change 754. If the FHR was in the "normal" range with normal variability and absent periodic change, [the maternal blood pressure (BP), check for low uterine activity, and evaluate fetus for position change 756.] A determination is made whether the low FHR persists 760. If yes, the baby is delivered 762. If the low FHR does not persist, the mother and fetus are closely observed 764.

If the previous baseline FHR was not in the "normal" range with normal variability and absent periodic change, the patient is hydrated with an IV bolus 758. A determination is made whether the low FHR persists 760. If yes, the baby is delivered 762. If the low FHR does not persist, the mother and fetus are closely observed 764. If the FHR was not in the "normal" range with normal variability and absent periodic change 754, the patient is hydrated and a determination is made whether the low FHR persists 760. If yes, the baby is delivered 762. If the low FHR does not persist, the mother and fetus are closely observed 764.

Figure 7E:

Referring now to FIG. 7E, in the cases where FHR is evaluated for periodic changes (FIGS. 7B and 7C), if early deceleration of FHR before contraction is determined 766, the patient is observed for any changes 776. If there is determined to be a late deceleration in FHR 768, fetal wellbeing is assessed or the fetus is delivered 774. If there is a variable deceleration of FHR 770, fetal wellbeing is assessed or the fetus is delivered 774. If there is an accelaertaion of FHR 772, the patient is observed for any further changes 776.

Referring again to FIGS. 1 and 2, the remote command center comprises an A/V conferencing server 190. In an embodiment of the present invention, A/V conferencing server 190 acquires audio and video signals from patient monitoring station "A" and provides a terminal (not shown) access to these signals via external network access 195. In yet another embodiment of the present invention addition, a local terminal (not shown) operated by a "local visitation participant" or "LVP" and a remote terminal (not shown) operated by a "remote visitation participant" or "RVP" are bridged by A/V conferencing server 190 to provide audio and video signals from the patient monitoring station, the local terminal and the remote terminal available simultaneously to LVP and RVP. Additionally, a terminal user may control the position of camera 205. By way of illustration and not as a limitation, RVPs may be family members or other concerned parties while LVPs may be patients, nurses, doctors, family members or other concerned parties. This embodiment thus permits family members the capability to "virtually visit" other sick family members when a physical visit to a patient's location is not possible and/or desirable. The "virtual visit" further allows the possibility to see and speak with a care provider regarding a patient's care or related subjects without having to be physically located at the health care provider's location. The present invention also provides a means for the floor staff (i.e. those caregivers in the hospital at or near the patient's bedside) to instantly alert the command center of the conditions of patients who destabilize thereby allowing for more rapid response by those manning the command center.

When each command center person logs onto the system of the present invention, a background service is started. This service subscribes to an emergency alert server that is connected to a video server. As noted earlier, the video server provides video feed from each beside to the command center as needed. Emergency message are passed from the bedside through the video server to the command center. As the emergency alert server receives a message from a video server, it sends a message to all of the subscribed services in the command center. This notification alerts the command center users by means of a "pop-up" alert window at the users' workstation that an emergency condition exists at the bed calling for the alert, and that the floor caregiver has requested immediate backup.

To facilitate the emergency call capability of the present invention, in addition to the various network connections of a more automated type, an emergency "call button" is provided at each critical care location. This could by or near each bed, at a nurse's station, at a mobile care bed or any location where the patient may be located. When pressed, the call button causes a message to be sent to the emergency alert server at the command center that a patient emergency has occurred.

The present invention comprises a video/audio server (Axis 2401) dedicated to each critical care location. A button activation mechanism and associated wiring is provided to allow the call button to be positioned in the room at a location convenient to the caregiver calling for command center backup.

Currently each video server can support up to 16 call buttons by using combinations of the four inputs to signify one alarm in a 4-bit binary pattern although this is not meant as a limitation. A typical installation would use one button or perhaps two (e.g. two beds per room) per video server.

A software interrupt event handler is configured on the video server to respond to activation of the emergency call button.

The emergency alert server comprises a web service called for sending emergency alert signals that is placed in service at system startup. When called, emergency alert web service responds with an acknowledgement message (e.g. "Alert Received"). The emergency alert web service identifies the ward and bed directly from the IP address (unique to each video server) and input number it was passed. It then sends a message to all subscribing clients identifying the emergency condition, the ward, and bed.

When a user logs into a workstation at the command center a user alert service subscribes to the emergency alert server and waits for any emergency message in the background. Upon receiving an emergency message, the service will popup a window with the message on top of the desktop and stay there until the user dismisses or acknowledges the alert. The user alert service the loads video assessment module to allow the command center to view the bed with the emergency.

In another embodiment of the present invention, a critical care hospital bed comprises monitoring instruments linked to a wireless network. This serves the needs of those patients who are transported from one location to another (either internal to a hospital or to other hospitals or diagnostic centers) for testing, procedures or other reasons. In this embodiment, monitoring continues using typical monitoring means that have been described above which include, without limitation, physiological monitoring equipment, video monitoring equipment and an emergency call button, all of which transmit their signals in a wireless fashion so that movement of the patient bed does not interrupt the transmission of information.

A telecommunications network for remote patient monitoring has now been illustrated. It will be apparent to those skilled in the art that other variations of the present invention are possible without departing from the scope of the invention as disclosed. For example, one can envision different ratios of remote command center to patient monitoring stations. Certain types of decision support algorithms would be used by intensivists, other types of remote monitoring of not only patient monitoring stations but other types of hospital functions as well as industrial functions where critical expertise is in limited supply but where that expertise must be applied to ongoing processes. In such cases a system such as that described can be employed to monitor processes and to provide standardized interventions across a number of locations and operations. Further, any reference to claim elements in the singular, for example, using the articles "a," "an," or "the" is not to be construed as limiting the element to the singular.

What is claimed is:

1. A rules-based system for maternal-fetal care of pregnant patients comprising:
   a network;
   a plurality of pregnant patient monitoring stations configured to monitor patient data elements from the pregnant patients, wherein the monitored patient data elements comprise data elements indicative of medical conditions of the pregnant patients and fetuses carried by the pregnant patients (hereinafter, "fetal patients");
   wherein each pregnant patient monitoring station comprises a communications interface that transmits tile monitored patient data elements to a remote command center via the network; and
   a remote command center connected to the network, wherein the remote command center comprises a rules engine, wherein the rules engine comprises rules tailored to the medical condition of a patent, and wherein the rules engine comprises instructions which when executed by the remote command center cause the remote command center to:
   receive the pregnant patient data elements;
   acquire other patient data elements, wherein the other patient data elements are indicative of the medical conditions of the pregnant patients and their fetal patients, and wherein the monitored patient data elements and the other patient data elements are collectively referred to as "pregnant patient data elements";

utilize the rules engine to apply rules tailored to the medical condition of a patient to at least two pregnant patient data elements;

determine when the conditions of any one of the rules tailored to the medical condition of the pregnant patients have been satisfied; and when the conditions of the any one of the rules tailored to the medical condition of the pregnant patients have been satisfied, take an action in accordance with the rule with respect to a particular one of the pregnant patients to whom the rule applies, and wherein the monitoring and determining when the conditions of the any one of the rules tailored to the medical condition of the pregnant patient has been satisfied occurs in an automated fashion at the remote command center according to the rules of the rules engine whenever the rules engine is in operation.

2. The system of claim 1, wherein when the satisfaction of the conditions of the rule tailored to the medical condition of the pregnant patient indicates that intervention in the treatment of the pregnant patient is warranted, then the action comprises issuing a mother alert.

3. The system of claim 1, wherein when the satisfaction of the conditions of the rule tailored to the medical condition of the pregnant patient indicates that intervention in the treatment of the fetal patient is warranted, then the action comprises issuing a fetal alert.

4. The system of claim 1, wherein a rule tailored to the medical condition of the pregnant patient comprises conditions to establish the medical condition of the pregnant patient.

5. The system of claim 1, wherein a rule tailored to the medical condition of the pregnant patient comprises conditions to establish the medical condition of the fetal patient.

6. The system of claim 1, wherein a rule tailored to the medical condition of the pregnant patient comprises an algorithm.

7. The system of claim 1, wherein the at least two pregnant patient data elements are selected from the group consisting of a physiological data element of the pregnant patient, a clinical data element of the pregnant patient, a medication data element of the pregnant patient, a laboratory data element of the pregnant patient, a physiological data element of the fetal patient, a clinical data element of the fetal patient, a medication data element of the fetal patient, and a laboratory data element of the fetal patient.

8. The system of claim 1, wherein the satisfaction of the any one of the rules tailored to the medical condition of the pregnant patient is indicative of a risk to the pregnant patient that does not pose a risk to the fetal patient.

9. The system of claim 1, wherein the satisfaction of the any one of the rules tailored to the medical condition of the pregnant patient is indicative of a risk to the pregnant patient and to the fetal patient.

10. The system of claim 1, wherein satisfaction of the any one of the rules tailored to the medical condition of the pregnant patient is indicative of a risk to the fetal patient that does not pose a risk to the pregnant patient.

11. The system of claim 1 wherein the pregnant patient monitoring stations comprise:

pregnant patient monitoring equipment, wherein the pregnant patient monitoring equipment comprises instructions which when executed by the pregnant patient monitoring equipment cause the pregnant patient monitoring equipment to monitor pregnant patient data elements from the pregnant patient and to send the monitored pregnant patient data elements to the remote command center via the network; and fetal patient monitoring equipment, wherein the fetal patient monitoring equipment comprises instructions which when executed by the fetal patient monitoring equipment cause the fetal patient monitoring equipment to monitor fetal patient data elements from the fetal patient and to send the monitored fetal patient data elements to the remote command center via the network.

12. The system of claim 1 further comprising a wireless subnetwork connected to the network and wherein the pregnant patient monitoring stations comprise;

pregnant patient monitoring equipment, wherein the pregnant patient monitoring equipment comprises instructions which when executed by the pregnant patient monitoring equipment cause the pregnant patient monitoring equipment to monitor pregnant patient data elements from the pregnant patient;

fetal patient monitoring equipment, wherein the fetal patient monitoring equipment comprises instructions which when executed by the fetal patient monitoring equipment cause the fetal patient monitoring equipment to monitor fetal patient data elements from the fetal patient;

a wireless interface connected to the wireless subnetwork, wherein the wireless interface comprises instructions which when executed by the wireless interface cause the wireless interface to:

receive the monitored pregnant patient data elements and the monitored fetal patient data elements; and send the monitored pregnant patient data elements and the monitored fetal patient to the remote command center via the wireless subnetwork.

13. The system of claim 1 further comprising a patient rules generator, wherein the patient rules generator comprises instructions which when executed by the patient rules generator cause the patient rules generator to:

create the rule tailored to the medical condition of the pregnant patient;

acquire rules performance measures indicative of the ability of the rule tailored to the medical condition of the pregnant patient to predict the change in the condition of the pregnant patient and the fetal patient; and determine from the rules performance measures whether to revise the rule.

14. The system of claim 13, wherein the patient rules generator further comprises instructions which when executed by the patient rules generator cause the patient rules generator to:

access historical data, wherein the historical data comprises other patient data elements for a plurality of other patients and wherein the patient data elements of another patient are associated with an outcome of the other patient;

apply multivariate analyses to the historical data to produce a result that relates the other patient data elements, the rule tailored to the medical condition of the pregnant patient, and the other patient outcomes; and generate a rules performance measure by comparing the result to the rule.

15. The system of claim 13, wherein the rules performance measures are derived from information provided by health care providers.

16. The system of claim 14, wherein patient rules generator further comprises instructions which when executed by the patient rules generator cause the patient rules generator to generate a new rule tailored to the medical condition of the pregnant patient from the result.

17. The system of claim 13, wherein the patient rules generator further comprises instructions which when executed by the patient rules generator cause the patient rules generator to test the new rule against the historical data.

18. The system of claim 1, wherein the system further comprises a site assessment module, wherein the site assessment module comprises instructions which when executed by the site assessment module cause the site assessment module to:
receive site assessment data, wherein the site assessment data are indicative of the capability of a healthcare facility to provide diagnostic and treatment services to perinatological patients; and
determine from the site assessment data service level measures indicative of a capability of the healthcare facility to provide diagnostic and treatment services to perinatological patients; and
wherein the rules generator further comprises instructions which when executed by the patient rules generator cause the patient rules generator to:
receive service level measures; and
create the rule tailored to the medical condition of the pregnant patient so as to be consistent with the service level measures of the healthcare facility.

19. The system of claim 18, wherein the site assessment module further comprises instructions which when executed by the site assessment module cause the site assessment module to:
prompt a user for the site assessment data; and
determine the service level measures based on the user response.

20. The system of claim 18, wherein the healthcare facility is associated with a site assessment code and the site assessment module further comprises instructions which when executed by the site assessment module cause the site assessment module to:
acquire the site assessment code associated with the healthcare facility; and
determine the service level measures at least in part based on the site assessment code.

21. The system of claim 18, wherein the service level measures comprise:
an inventory of available monitoring data elements;
an inventory of available diagnostic services;
an inventory of available surgical treatment services;
an inventory of available perinatological treatment services; and
an inventory of available laboratory services.

22. The system of claim 1, wherein the network is selected from the group consisting of a wired network, a wireless network, a satellite network, a public switched telephone network, an IP network, a packet switched network, a cell phone network, a cable network, and a coax network, a hybrid fiber coax network.

23. A method for managing the care of pregnant patients from a remote command center comprising:
communicating over a network monitored patient data elements of the pregnant patients to the remote command center, wherein the remote command center comprises rules tailored to the medical condition of the pregnant patients;
at least one computer processor coupled to a datastore acquiring other patient data elements, wherein the other patient data elements are indicative of the medical conditions of the pregnant patients and their fetal patients, and wherein the monitored patient data elements and the other patient data elements are collectively referred to as "pregnant patient data elements"; and
the at least one computer processor using a rules engine to apply rules tailored to the medical condition of the pregnant patients rules to at least two pregnant patient data elements;
the at least one computer processor determining when the conditions of any one of the rules tailored to the medical condition of the pregnant patients have been satisfied; and
when the conditions of the any one of the rules tailored to the medical condition of the pregnant patients have been satisfied, taking an action in accordance with the rule with respect to a particular one of the pregnant patients to whom the rule applies, and
wherein the monitoring and determining when the conditions of the any one rule has been satisfied occurs in an automated fashion at the remote command center repeatedly and automatically according to the rules of the rules engine whenever the rules engine is in operation.

24. The method of claim 23, wherein when the satisfaction of the conditions of the rule tailored to the medical condition of the pregnant patient indicates that intervention in the treatment of the pregnant patient is warranted, then taking an action in accordance with the rule comprises issuing a mother alert.

25. The method of claim 23, wherein when the satisfaction of the conditions of the rule tailored to the medical condition of the pregnant patient indicates that intervention in the treatment of the fetal patient is warranted, then taking an action in accordance with the rule comprises issuing a fetal alert.

26. The method of claim 23, wherein a rule tailored to the medical condition of the pregnant patient comprises conditions to establish the medical condition of the pregnant patient.

27. The method of claim 23, wherein a rule tailored to the medical condition of the pregnant patient comprises conditions to establish the medical condition of the fetal patient.

28. The method of claim 23, wherein a rule tailored to the medical condition of the pregnant patient comprises an algorithm.

29. The method of claim 23, wherein at least two pregnant patient data elements are selected from the group consisting of a physiological data element of the pregnant patient, a clinical data element of the pregnant patient, a medication data element of the pregnant patient, and a laboratory data element of the pregnant patient, a physiological data element of the fetal patient, a clinical data element of the fetal patient, a medication data element of the fetal patient, and a laboratory data element of the fetal patient.

30. The method of claim 23, wherein satisfaction of the any one of the rules tailored to the medical condition of the pregnant patient is indicative of a risk to the pregnant patient that does not pose a risk to the fetal patient.

31. The method of claim 23, wherein satisfaction of the any one of the rules tailored to the medical condition of the pregnant patient is indicative of a risk to the pregnant patient and to the fetal patient.

32. The method of claim 23, wherein satisfaction of the any one of the rules tailored to the medical condition of the pregnant patient is indicative of a risk to the fetal patient that does not pose a risk to the pregnant patient.

33. The method of claim 23, communicating over a network monitored patient data elements of the pregnant patients to the remote command center comprises:

receiving pregnant patient data elements from pregnant patient monitoring equipment associated with the pregnant patient;

sending the monitored pregnant patient data elements to the remote command center via the network;

receiving fetal patient data elements from fetal patient monitoring equipment associated with the fetal patient; and sending the monitored fetal patient data elements to the remote command center via the network.

34. The method of claim 23, wherein communicating over a network monitored patient data elements of the pregnant patients to the remote command center comprises:

sending pregnant patient data elements from pregnant patient monitoring equipment associated with the pregnant patient to a wireless interface;

sending fetal patient data elements from fetal patient monitoring equipment associated with the fetal patient to the wireless interface; and sending the monitored pregnant patient data elements and the monitored fetal patient from the wireless interface to the network via a wireless subnetwork.

35. The method of claim 23, further comprising:

creating the rule tailored to the medical condition of the pregnant patient;

acquiring rules performance measures indicative of the ability of the rule to predict the change in the condition of the pregnant patient and the fetal patient; and determining from the rules performance measures whether to revise the rule.

36. The method of claim 35 further comprising:

accessing historical data, wherein the historical data comprises other patient data elements for a plurality of other patients and wherein the patient data elements of another patient are associated with an outcome of the other patient;

applying multivariate analyses to the historical data to produce a result that relates the other patient data elements, the rule tailored to the medical condition of the pregnant patient, and the other patient outcomes; and generating a rules performance measure by comparing the result to the rule tailored to the medical condition of the pregnant patient.

37. The method of claim 35, wherein the rules performance measures are derived from information provided by health care providers.

38. The method of claim 36, further comprising generating a new rule tailored to the medical condition, of the pregnant patient from the result.

39. The method of claim 35, further comprising testing the new rule against the historical data.

40. The method of claim 23, further comprising:

receiving site assessment data, wherein the site assessment data are indicative of the capability of a healthcare facility to provide diagnostic and treatment services to perinatological patients;

determining from the site assessment data service level measures indicative of a capability of the healthcare facility to provide diagnostic and treatment services to perinatological patients; and creating the rule tailored to the medical condition of the pregnant patient so as to be consistent with the service level measures of the healthcare facility.

41. The method of claim 40, further comprising:

prompting a user for the site assessment data; and determining the service level measures based on the user response.

42. The method of claim 40, wherein the healthcare facility is associated with a site assessment code and the method further comprises:

acquiring the site assessment code associated with the healthcare facility; and determining the service level measures at least in part based on the site assessment code.

43. The method of claim 40, wherein the service level measures comprise:

an inventory of available monitoring data elements;

an inventory of available diagnostic services;

an inventory of available surgical treatment services;

an inventory of available perinatological treatment services; and an inventory of available laboratory services.

44. The method of claim 23, wherein the network is selected from the group consisting of a wired network, a wireless network, a satellite network, a public switched telephone network, an IP network, a packet switched network, a cell phone network, a cable network, and a coax network, a hybrid fiber coax network.

* * * * *